United States Patent [19]
van Lake

[11] Patent Number: 5,653,737
[45] Date of Patent: Aug. 5, 1997

[54] PROGRAMMABLE PACEMAKER FOR NONINVASIVE EP TESTING FOR ATRIAL TACHYCARDIAS WITH VENTRICULAR SUPPORT

[75] Inventor: Paul van Lake, Scottsdale, Ariz.

[73] Assignee: Pacesetter, Inc., Sylmar, Calif.

[21] Appl. No.: 629,284

[22] Filed: Apr. 8, 1996

[51] Int. Cl.$^6$ ................................................. A61N 1/362
[52] U.S. Cl. ............................ 607/9; 607/4; 128/697
[58] Field of Search ................................. 607/4, 5, 7, 9, 607/11, 15, 27; 128/697

[56] References Cited

U.S. PATENT DOCUMENTS

| | | | |
|---|---|---|---|
| 4,585,004 | 4/1986 | Brownlee | 607/27 |
| 4,705,043 | 11/1987 | Imran | 28/697 |
| 4,870,974 | 10/1989 | Wang | 607/27 |
| 5,129,392 | 7/1992 | Bardy et al. | 607/27 |
| 5,184,616 | 2/1993 | Weiss | 607/4 |
| 5,282,836 | 2/1994 | Kreyenhagen et al. | 607/4 |

OTHER PUBLICATIONS

Fletcher, M.D., Ross D., et al., "The Use of the Implanted Pacemaker as an In Vivo Electrophysiology Laboratory," *Journal of Electrophysiology*, vol. 1, No. 5, pp. 425–433 (1987).

Hassett, James A., et al., "Noninvasive Diagnosis and Treatment of Atrial Flutter Utilizing Previously Implanted Dual Chamber Pacemaker," *PACE*, vol. 11, Part II, pp. 1662–1666 (Nov. 1988).

Wish, Marc, et al., "A New Advancement in Noninvasive Electrophysiology: A Standard Laboratory Stimulator Pulse Coupled with an Implanted Pacemaker," *PACE*, vol. 9, Part II, pp. 1089–1094 (Nov.–Dec. 1986).

*Primary Examiner*—William E. Kamm
*Assistant Examiner*—George R. Evanisko

[57] ABSTRACT

A programmable pacemaker that allows both noninvasive electrophysiological ("EP") testing for atrial tachycardias and ventricular pacing support, by allowing operation in the atrial channel to be decoupled from operation in the ventricular is provided. Many patients require EP testing to evaluate a predisposition to tachycardias. Many of these patients also have dual-chamber pacemakers for cardiac support. These systems can be noninvasively coupled to a external programmer enabling the already implanted system to serve as an in vivo EP laboratory. When performing noninvasive atrial EP testing with current dual-chamber pacemakers, the device must first be programmed to a single-chamber triggered mode. The present system allows the pacemaker to maintain ventricular pacing during EP testing.

44 Claims, 3 Drawing Sheets

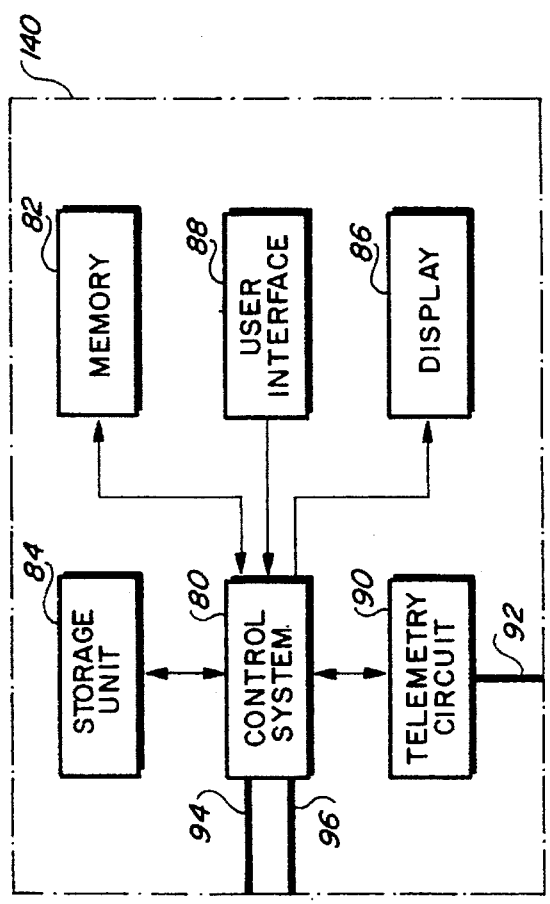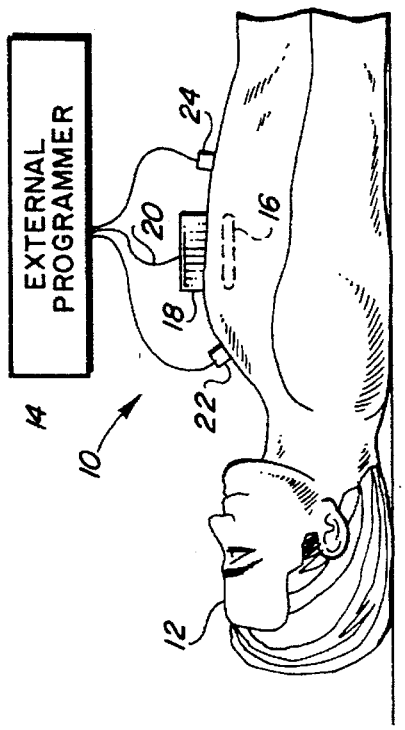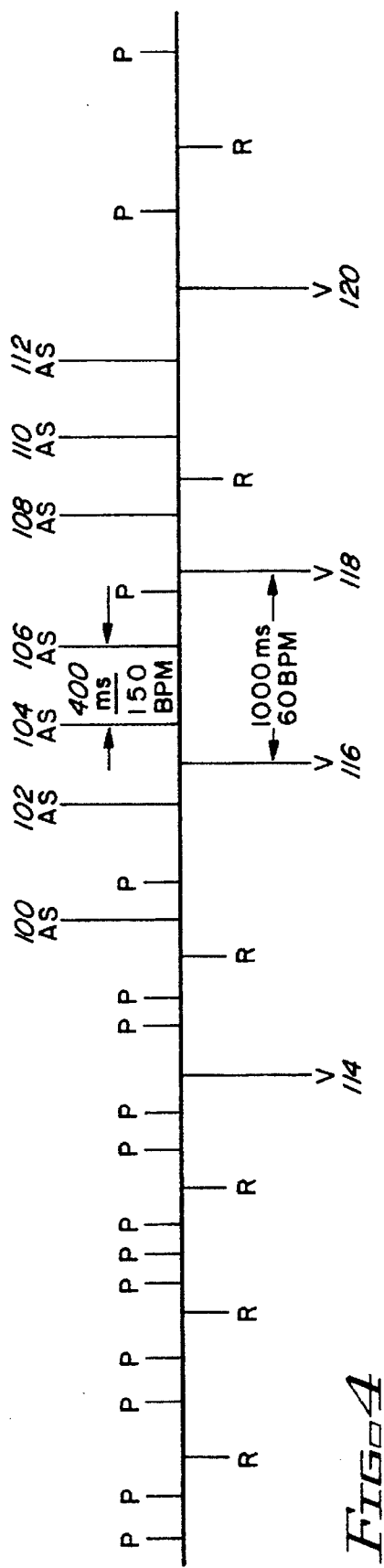
Fig. 3
Fig. 1
Fig. 4

PROGRAMMABLE PACEMAKER FOR NONINVASIVE EP TESTING FOR ATRIAL TACHYCARDIAS WITH VENTRICULAR SUPPORT

BACKGROUND OF THE INVENTION

The present invention relates generally to programmable implantable pacemakers, and particularly to implantable dual-chamber pacemakers used for performing noninvasive electrophysiological ("EP") testing. More particularly, the present invention relates to a dual-chamber pacemaker in which the atrial and ventricular channels can operate simultaneously yet independently so that, during noninvasive EP testing for atrial tachycardias, the device can generate bursts of pacing pulses to induce and terminate atrial arrhythmias, while maintaining ventricular pacing support.

EP testing is a procedure that is commonly used to evaluate an individual's susceptibility to cardiac arrhythmias, particularly atrial and ventricular tachycardias. EP testing is also used to determine whether or not a particular patient would respond favorably to various therapies, such as drug therapies and electrical stimulation therapies, that are often used to treat cardiac arrhythmias.

These objectives are typically accomplished by inducing arrhythmias at selected locations in the patient's heart through the use of "bursts" of electrical stimulation. The stimulation bursts are applied to the patient's heart in a sequence that is known to induce the desired arrhythmia.

Once an arrhythmia has been induced, electrical stimulation and/or drug therapy may be used to attempt to revert the arrhythmia. For example, another burst of electrical stimulation may be applied to the patient's heart in a sequence that is known to be successful in reverting arrhythmias. Alternatively, a drug may be administered to attempt to return the patient's heart rhythm back to normal. In addition, EP testing can be used to evaluate the effectiveness of preventative measures, such as drugs that are intended to reduce susceptibility to cardiac arrhythmias in patients who may be predisposed to such episodes. Thus, EP testing allows a physician to prescribe a course of therapy that is specifically tailored to each patient's condition.

EP testing traditionally has been an invasive procedure. Specifically, surgery has been required to introduce electrical leads into the patient's body and to guide the electrode tips of the leads to a desired location in the patient's heart. The leads are coupled to an external EP stimulator which is used by the physician to control the intensity and sequence of electrical stimulation that is delivered to the patient's heart.

Surgery, of course, is not without risks. In the case of invasive EP testing, certain patients may occasionally experience thrombosis, bleeding or infection. Not surprisingly, alternatives to invasive EP testing were sought.

It has been found that noninvasive EP testing can be performed on patients who have received pacemakers to treat bradycardia (slow heart rate). Essentially, the implanted pacemaker, when properly configured, can be used as an in vivo EP testing laboratory. This is typically accomplished by configuring the pacemaker, using an external programming unit, to generate and administer bursts of pacing pulses in a sequence that induces or reverts the desired arrhythmia. Noninvasive EP testing can be used for most tests that are performed through invasive EP testing.

A detailed description of some of the different approaches to noninvasive EP testing, and their respective advantages and disadvantages, may be found in Fletcher, R. D. et al., "The Use of the Implanted Pacemaker as an In Vivo Electrophysiology Laboratory," *Journal of Electrophysiology*, Vol. 1, No. 5, 1987. In one approach known as "triggered," an EP stimulator is used to apply external, chest wall stimulation to a patient undergoing EP testing. With this approach, the implanted pacemaker is set to a triggered mode of operation (e.g., AAT for atrial testing or VVT for ventricular testing). The chest wall stimulation is applied in a burst sequence designed to either induce or revert an arrhythmia, but at an energy level that is not uncomfortable for the patient. Each stimulation pulse in the burst triggers the implanted pacemaker to administer a pacing pulse. The pacemaker thus tracks the burst sequence of the EP stimulator.

In a second approach known as "indirect," an EP stimulator is coupled to a pacemaker programmer, which in turn is set up to communicate telemetrically with the implanted pacemaker. The programmer maintains a radio frequency link to the pacemaker during the test, except when the EP stimulator sends a pulse to the programmer. When a pulse is sent, the programmer breaks the radio frequency link which causes the pacemaker (which is typically set to the AAI or VVI mode) to administer a pacing pulse. The EP stimulator can thus cause the pacemaker to deliver pulses in a desired burst sequence by sending signals to the programmer in the appropriate sequence.

A third approach known as "direct" does not require an EP stimulator. With this approach, the physician can control the pacemaker burst sequences by using a pacemaker programmer that includes software that is specifically designed for EP testing. When this approach is used, the physician typically first disables pacing support in the chamber that is not to be tested. The physician then uses the programmer to send commands to the pacemaker to cause the pacemaker to administer burst stimulation in a desired sequence to either induce or revert an arrhythmia.

Regardless of the approach used, noninvasive EP testing can be a highly desirable alternative to invasive EP testing. Unfortunately, however, atrial EP testing does not accommodate patients who may require back-up ventricular pacing during the EP test, even if the patient is equipped with a dual-chamber pacemaker. This is because the pacemaker is generally set to a single-chamber mode of operation prior to EP testing. This may be done by setting the pacemaker to AAI or AAT mode (depending on the approach being used to perform EP testing), or by setting the pacing parameters in the non-tested chamber (in this case, the ventricle) to prevent effective pacing pulses from being delivered (e.g., by extending the refractory period or by setting the output energy to below threshold). Dual-chamber pacemakers have generally been set to a single-chamber mode during EP testing in order to prevent high-rate pacing in one chamber (e.g., the atrium) during EP testing from causing the other chamber (e.g., the ventricle) to follow the high-rate activity, because inappropriate pacing of the other chamber may cause pacemaker-induced arrhythmia. Thus, with current dual-chamber pacemakers, if the pacemaker is set to perform EP testing in the atrium, then no ventricular pacing (or ventricular sensing) is provided.

Patients who lack sufficient AV conduction require back-up ventricular pacing during atrial EP testing. Previously known techniques for providing back-up ventricular pacing during atrial EP testing require the insertion of invasive leads into the patient to pace the ventricle.

Thus, it would be desirable for an implanted pacemaker capable of operating in an EP testing mode to provide back-up ventricular pacing support during atrial EP testing. It would also be desirable for the pacemaker to allow operation of the atrial channel involved in EP testing to be decoupled from the operation of the ventricular channel involved in ventricular pacing. It would further be desirable for the pacemaker to allow the physician to set pacemaker parameters for the atrial channel independent of the pacemaker parameters for the ventricular channel, so that the pacemaker can simultaneously perform atrial EP testing and provide optimal ventricular pacing support.

SUMMARY OF THE INVENTION

The disadvantages and limitations discussed above are overcome by the present invention. In accordance with this invention, a new implantable dual-chamber pacemaker is provided, which can be programmed to simultaneously operate in one mode in an atrial channel (e.g., an atrial EP testing mode) and in a different, independent mode in a ventricular channel (e.g., a ventricular pacing mode).

The present invention thus provides an implantable pacemaker that can maintain back-up ventricular pacing support during atrial EP testing.

The pacemaker of the present invention includes a control system for controlling the operation of the pacemaker, a set of leads for receiving atrial and ventricular signals and for delivering atrial and ventricular stimulation pulses, a set of amplifiers for amplifying the atrial and ventricular signals, and pulse generators for generating atrial and ventricular stimulation pulses. In addition, the pacemaker includes memory for storing operational parameters for the control system and for storing data acquired by the control system for later retrieval by the medical practitioner using an external programmer. The pacemaker also includes a telemetry circuit for communicating with the external programmer.

Unlike previously known dual-chamber pacemakers, the pacemaker of the present invention allows simultaneous operation in an atrial EP testing mode and a ventricular pacing mode. When programmed according to the present invention, the pacemaker can provide ventricular pacing support while EP burst sequences are directed to the atrial chamber under the control of a pacemaker programmer that is configured to control the pacemaker in an EP testing mode. The ventricular channel can be programmed to operate in VVI or VOO mode during atrial EP testing to provide either demand or asynchronous ventricular pacing support with parameters deemed appropriate by the physician. The pacing parameters may be programmed into the pacemaker independent of any EP testing parameters that may be set by the physician. These parameters may include pulse width, pulse amplitude, pacing rate and amplifier sensitivity, among others.

In the preferred embodiment of the present invention, the pacemaker is configured to operate as though the atrial channel (operating in EP testing mode) is decoupled from the ventricular channel (operating in single-chamber pacing mode). Atrial events that occur during EP testing do not affect the operation of the ventricular channel. The ventricular channel paces the ventricular chamber independently while the atrial channel is used with the programmer for EP testing according to input provided by the physician. For example, the pacemaker can operate in AAT burst-pacing mode to revert atrial tachycardias in the atrial chamber and simultaneously in VVI mode to provide ventricular pacing support in the ventricular chamber.

With respect to VVI mode, the ventricular sensor can be adjusted to avoid inappropriate interpretation of atrial pulses as intrinsic ventricular activity due to cross-talk. Desensitizing the ventricular sensor to atrial activity, in addition to decoupling the channels, helps prevent inappropriate inhibition of ventricular output.

In another aspect of the invention, a method of performing EP testing in an atrial chamber of the heart and simultaneously providing ventricular pacing support using an implanted pacemaker is provided.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which:

FIG. 1 generally depicts a patient undergoing noninvasive EP testing in accordance with the principles of the present invention;

FIG. 3 is a block diagram of a programmer that can be used with the pacemaker of FIG. 1 in accordance with the principles of the present invention;

FIG. 4 is a timing waveform annotated with marker channel data illustrating the atrial and ventricular pulses delivered as well as the intrinsic atrial and ventricular contractions sensed by the pacemaker in accordance with the principles of the present invention.

DETAILED DESCRIPTION OF THE PREFERRED EMBODIMENT

Figure 2:
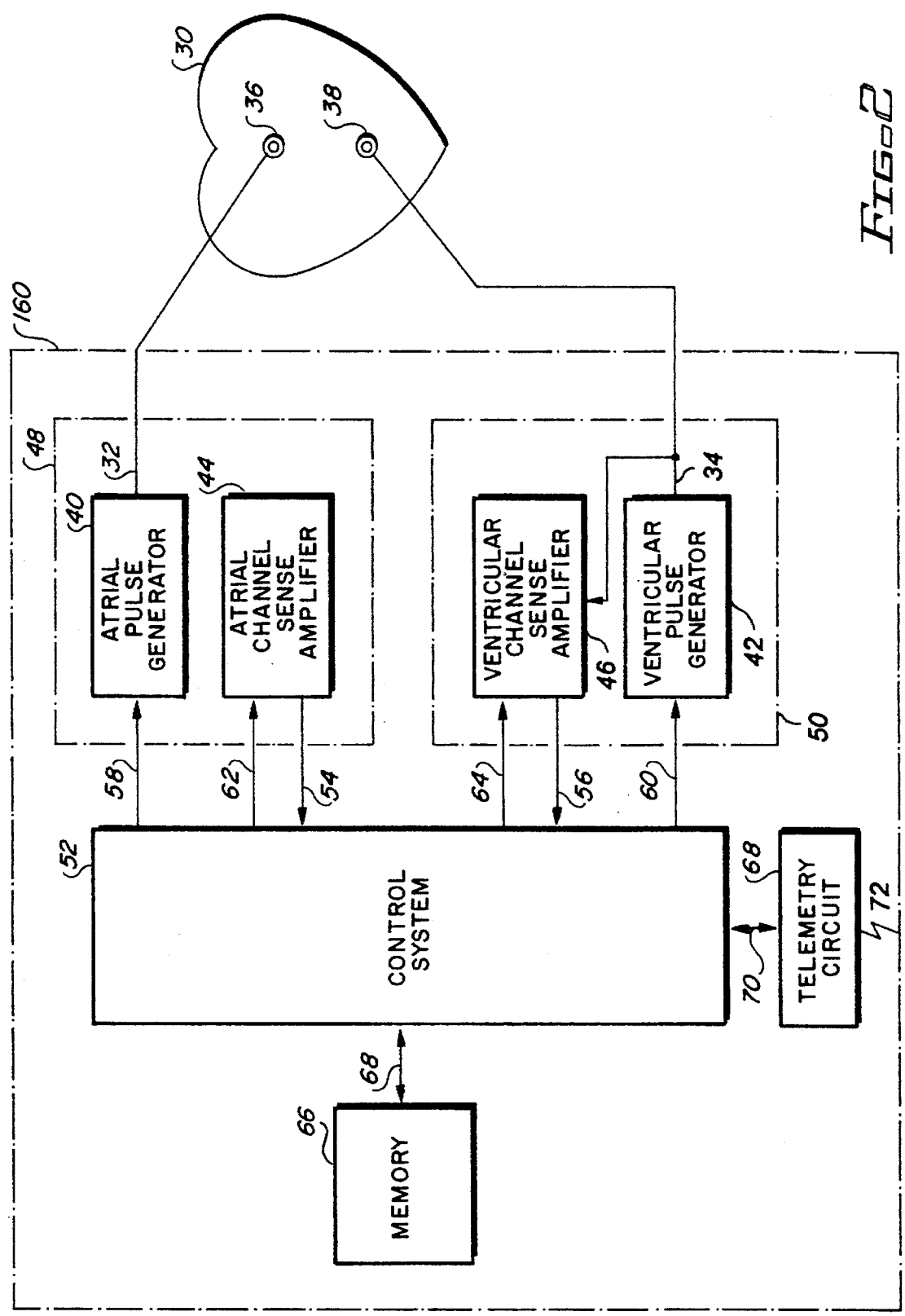
FIG. 2 is a block diagram of a pacemaker that can simultaneously perform atrial EP testing and provide ventricular pacing support in accordance with the principles of the present invention.

Referring first to FIG. 1, a generalized arrangement of a noninvasive EP testing system 10 is described. The EP testing system 10 may be used to simultaneously perform atrial EP testing on, and provide bradycardia pacing support to, a patient 12 in accordance with the principles of the present invention.

In broad terms, the EP testing system 10 includes an external programmer 14 and a pacemaker 16 implanted in the patient 12. The programmer 14 communicates with the pacemaker 16 via a telemetry head 18 which is coupled to the programmer using a suitable connecting cable 20. The telemetry head 18 is typically placed on the chest of the patient 12 in the vicinity of the pacemaker 16 in order to insure a reliable RF connection.

Preferably, the EP testing system 10 includes at least a pair of electrodes 22 and 24 which are used by the programmer 14 to monitor the electrocardiogram ("ECG") of the patient 12 undergoing EP testing. The ECG provides the physician with important information concerning the patient's condition during EP testing. Other important diagnostic information, such as the intracardiac electrogram ("IEGM") of the patient 12 and marker channel data, may be transmitted from the pacemaker 16 to the programmer 14 via the telemetry head 18 and the cable 20.

The EP testing system 10 as shown in FIG. 1 is arranged in the "direct" configuration. In the direct configuration, the programmer 14 can cause the pacemaker 16 to deliver EP testing stimulation bursts upon receiving the appropriate commands from the physician, without the need for an external EP stimulator (not shown). Those of ordinary skill in the art will understand, however, that the principles of the present invention may be practiced using other suitable EP testing configurations, including at least the "indirect" and "triggered" configurations.

Referring now to FIG. 2, a pacemaker 160 is described which is suitable for use as the pacemaker 16 of the EP testing system 10 shown in FIG. 1. In accordance with the principles of this invention, the pacemaker 160 is capable of performing atrial EP testing while maintaining ventricular pacing support.

The pacemaker 160 is coupled to the patient's heart 30 by way of a pair of leads 32 and 34, the lead 32 having an electrode 36 which is in contact with one of the atria of the heart 30, and the lead 34 having an electrode 38 which is in contact with one of the ventricles. The lead 32 carries stimulating pulses to the electrode 36 from an atrial pulse generator 40, while the lead 34 carries stimulating pulses to the electrode 38 from a ventricular pulse generator 42. In addition, electrical signals from the atria are carried from the electrode 36, through the lead 32 to an input terminal of an atrial sense amplifier 44. Electrical signals from the ventricles are carried from the electrode 38, through the lead 34 to an input terminal of a ventricular sense amplifier 46. The atrial pulse generator 40, atrial sense amplifier 44 and lead 32 may be viewed collectively as an atrial channel 48. Similarly, the ventricular pulse generator 42, ventricular sense amplifier 46 and lead 34 may be viewed collectively as a ventricular channel 50.

Although the pacemaker 160 is shown in FIG. 2 as having two pulse generators (one each for the atrium and the ventricle), it should be noted that the invention can be practiced using other pacemaker embodiments. For example, a single pulse generator may be used with suitable switching circuitry (not shown).

Controlling the dual-chamber pacemaker 160 is a control system 52, which is preferably microprocessor-based. The control system 52 also includes a real-time clock (not shown) for providing timing for monitoring cardiac events and for timing the application of stimulation pulses by the pulse generators 40 and 42.

The control system 52 receives the output signals from the atrial amplifier 44 over a signal line 54. Similarly, the control system 52 receives the output signals from the ventricular amplifier 46 over a signal line 56. These output signals are generated each time that an atrial event (e.g., a P-wave) or a ventricular event (e.g., an R-wave) is sensed within the heart 30.

The control system 52 also generates an atrial trigger signal which is sent to the atrial pulse generator 40 over a signal line 58, and a ventricular trigger signal which is sent to the ventricular pulse generator 42 over a signal line 60. The appropriate trigger signal is generated each time that a stimulation pulse is to be generated by one of the pulse generators 40 or 42. The atrial stimulation pulse is referred to simply as the "A-pulse," and the ventricular stimulation pulse is referred to as the "V-pulse."

During the time that either an A-pulse or a V-pulse is being delivered to the heart 30, the corresponding atrial amplifier 44 or the ventricular amplifier 46 is typically disabled by way of a blanking signal presented to the appropriate amplifier from the control system 52 over a signal line 62 for the atrial amplifier 44 or a signal line 64 for the ventricular amplifier 46. This blanking action prevents the amplifiers 44 and 46 from becoming saturated with the relatively large stimulation pulses which are present at their input terminals during pacing pulse delivery. This blanking action also prevents residual electrical signals (known as "after-potentials") present in the muscle tissue as a result of the pacemaker stimulation from being interpreted as atrial or ventricular events.

Still referring to FIG. 2, the pacemaker 160 also includes a memory circuit 66 which is coupled to the control system 52 through a suitable data bus 68. The memory circuit 66 allows certain control parameters used by the control system 52 in controlling the operation of the pacemaker 160 to be programmably stored and modified, as required, in order to customize the operation of the pacemaker 160 to suit the needs of a particular patient. These parameters may include, for example, pulse width, pulse amplitude, pacing rate, blanking interval and amplifier sensitivity, among others.

Advantageously, the pacemaker 160 of the present invention can store different sets of control parameters in the memory 66 for use in controlling different modes of operation. For example, the parameters for controlling the atrial channel 48 during EP testing may differ from the parameters used to control the atrial channel 48 during bradycardia pacing. In addition, the parameters used by the control system 52 to control bradycardia pacing by the ventricular channel 50 during atrial EP testing may differ from those used to control the ventricular channel at other times.

Data sensed during the operation of the pacemaker 160 (e.g., marker channel and IEGM data) may be stored in the memory circuit 66 for later retrieval and analysis.

A telemetry circuit 68 is also included in the pacemaker 160. The telemetry circuit 68 is connected to the control system 52 by way of a suitable command/data bus 70. In turn, the telemetry circuit 68 may be selectively coupled to the external programmer 14 (FIG. 1) by means of an appropriate communication link 72. The communication link 72 may be any suitable electromagnetic link such as an RF (radio frequency) channel.

Commands may be sent by the medical practitioner to the control system 52 from the external programmer 14 (FIG. 1) through the communication link 72. Similarly, through this communication link 72 and the external programmer 14 (FIG. 1), data (either held within the control system 52 (as in a data latch) or stored within the memory circuit 66), may be remotely transmitted by the pacemaker 160 to the external programmer 14 (FIG. 1). In this manner, noninvasive communication may be established with the implanted pacemaker 160 from a remote location.

The operation of the pacemaker 160 is generally controlled by a control program stored in the memory circuit 66 and executed by the control system 52. This control program usually consists of multiple integrated program modules, with each module bearing responsibility for controlling one or more functions of the pacemaker 160. For example, one program module may control the delivery of stimulating pulses to the heart 30, while another module may control the acquisition of atrial and ventricular electrical signals. In effect, each program module is a control program dedicated to a specific function or a set of functions of the pacemaker 160. As described in greater detail below, a particular control program module is used by the control system 52 to enable the pacemaker 160 to perform atrial EP testing while maintaining ventricular pacing support.

Referring now to FIG. 3, an external programmer 140 is described which may be used as the external programmer 14 of the EP testing system 10 shown in FIG. 1. In particular, the programmer 140 may be used to program the pacemaker 16 (FIG. 1) to perform noninvasive atrial EP testing while maintaining ventricular pacing support.

The programmer 140 is controlled by a control system 80, which is preferably microprocessor-based. The control system 80 executes control program instructions that it reads from a memory circuit 82. Upon start-up, the control system 80 loads the memory circuit 82 with at least a portion of a control program that is stored in a nonvolatile storage unit 84. The storage unit 84 may be, for example, a hard disk, although other suitable nonvolatile storage devices may be used instead.

By executing the control program stored in the memory circuit 82, the control system 80 is able to present a series of menus on a display 86. The physician can make selections from the menus through the use of a user interface 88. The user interface 88 may be a keyboard, mouse, touch-screen, light pen, digitizer or any other suitable input device that allows the physician to make choices from the menus displayed on the display 86.

Some of the menus presented by the control system 80 on the display 86 allow the physician to configure the pacemaker 160 (FIG. 2) for noninvasive EP testing. The configuration instructions provided by the physician through the user interface 88 are interpreted by the control unit 80 and transmitted to the pacemaker 160 (FIG. 2) through use of a telemetry circuit 90 and a cable 92 (corresponding to the cable 20 of FIG. 1).

The programmer 140 is used initially by the physician to reconfigure the pacemaker 160 (FIG. 2) from its ordinary mode of operation (e.g., dual chamber bradycardia pacing) to the EP testing mode of the present invention. The instructions sent by the programmer 140 to the pacemaker 160 (FIG. 2) may include the ventricular pacing mode to be used while atrial EP testing is being performed (e.g., VVI, VVT, VOO). The instructions may also include separate sets of pacing parameters for the atrial channel 48 (FIG. 2) and the ventricular channel 50 (FIG. 2). These parameters may include pulse width, pulse amplitude, pacing rate, blanking interval and amplifier sensitivity, among others. Ventricular pacing parameters may be needed in addition to the atrial EP testing parameters, because it may be desirable to use a different set of parameters for ventricular pacing during EP testing than are used during ordinary dual-chamber operation of the pacemaker 160 (FIG. 2). In particular, if VVI pacing is to be used, it may be desirable to decrease the sensitivity of the ventricular sense amplifier 46 (FIG. 2) in order to avoid sensing of the stimulation pulses delivered by the atrial pulse generator 40 (FIG. 2) during EP testing.

The programmer 140 is also used by the physician to define the burst sequences to be used during atrial EP testing. Different burst sequences may thus be administered by the pacemaker 160 (FIG. 2) to induce and revert atrial arrhythmias.

The programmer 140 is also used to receive information from the pacemaker 160 (FIG. 2) during noninvasive EP testing. For example, the programmer 140 may receive through the cable 92 and telemetry circuit 90, marker channel and IEGM data sent by the pacemaker 160 (FIG. 2). In addition, the patient's ECG may be obtained through the electrodes 94 and 96 (corresponding to the electrodes 22 and 24 of (FIG. 1). Advantageously, the data received by the programmer 140 represents cardiac activity in both the atrial chamber undergoing EP testing and the ventricular chamber that receives bradycardia pacing support during EP testing of the atrial chamber.

When EP testing is complete, the physician uses the programmer 140 to instruct the pacemaker 160 (FIG. 2) to return to its original, dual-chamber mode of operation.

Referring again to FIG. 2, during EP testing, the atrial pulse generator 40 generates pulses as directed by the control system 52 of the pacemaker 160, which in turn is directed by the external programmer 140 (FIG. 3) through the telemetry circuit 72. Bursts of pacing pulses delivered in a prescribed sequence to the atrium of the heart 30 may be used to induce an atrial arrhythmia. Another burst sequence can then be used to revert the arrhythmia to sinus rhythm.

Operation of the ventricular channel 50 proceeds according to the mode of operation programmed by the physician using the programmer 140 (FIG. 3). In one embodiment of the present invention, the ventricular channel 50 operates in VOO mode. The ventricular pulse generator 42 provides asynchronous, back-up pacing support regardless of any atrial activity that occurs during EP testing. The ventricular pacing rate is determined by the physician depending on the patient's needs. A relatively high pacing rate may be required by some patients, whereas for other patients, a high pacing rate can cause pacemaker-induced tachycardia.

In an alternative embodiment, the ventricular channel 50 operates in VVI mode, providing ventricular pacing support only as needed by the patient (i.e., in the absence of intrinsic ventricular activity). If the patient's intrinsic rhythm is faster than the programmed pacing rate of the pacemaker 160, then the ventricular pulse generator 42 is inhibited.

The ventricular channel 50 can alternatively operate in VVT mode. In VVT mode, however, the ventricular pulse generator 42 paces the ventricular chamber even if the intrinsic rate is higher than the programmed pacing rate for the ventricular channel 50.

VVI pacing is preferred over VVT pacing for several reasons. First, VVI mode conserves energy and thus increases the life of the battery (not shown) of the pacemaker 160. VVT mode depletes the battery more rapidly than VVI mode because VVT mode stimulates the heart even when the intrinsic rate exceeds the programmed pacing rate. Second, VVI mode presents an undistorted, intrinsic QRS complex, which facilitates the evaluation of the patient's symptoms. In VVT mode, each intrinsic QRS complex is distorted by a triggered, pacing artifact—thus limiting diagnostic utility. Third, VVT mode may cause ventricular pacing at undesired high rates.

The energy content of stimulation pulses administered to the atrium during EP testing may be higher than the energy content of atrial pacing pulses. These higher energy pulses may be sensed by the ventricular channel sense amplifier 46 and misinterpreted as intrinsic ventricular activity. The present invention provides at least two ways for addressing this concern. First, the sensitivity of the ventricular channel sense amplifier 46 can be reduced to decrease the likelihood of it sensing atrial events. Thus, the sensitivity of the ventricular channel sense amplifier 46 may be lower during atrial EP testing than it is at other times. Second, a post-atrial blanking signal can be sent to the ventricular channel sense amplifier 46 over the signal line 64 after each atrial pulse during the EP test. The blanking signal causes the ventricular channel sense amplifier 46 to become nonresponsive to cardiac signals for a period of time known as a "blanking interval." The duration of the blanking interval may be set by the physician using the programmer 140 (FIG. 3). The duration may vary depending upon testing conditions (e.g., the energy content of the atrial stimulation pulses) and the condition of the patient.

In an alternative embodiment of the present invention, the ventricular pacing rate can be a function of the atrial rate, rather than independent of atrial events. For example, the ventricular pacing rate can be derived from dividing down the atrial events.

FIG. 4 is a timing waveform illustrating an atrial EP test, during which a burst of atrial stimulation pulses is used by the pacemaker 160 (FIG. 2) to terminate an atrial tachycardia. The timing waveform of FIG. 4 is annotated with marker channel data showing a sequence of atrial EP testing stimuli (AS) 100, 102, 104, 106, 108, 110 and 112 and ventricular pacing pulses 114, 116, 118 and 120 as they would be generated by the pacemaker 160 (FIG. 2) during atrial EP testing in accordance with the principles of the present invention. It should be noted that the same principles apply when the pacemaker 160 (FIG. 2) is delivering EP testing stimuli to induce an arrhythmia in the atrium.

Through the telemetry circuit 68 (FIG. 2), the external programmer 140 (FIG. 3) provides the instructions necessary for the atrial pulse generator 40 to deliver the sequence of atrial stimuli 102, 104, 106, 108, 110 and 112 to terminate the atrial tachycardia. During the atrial EP test, the ventricular pacing pulses 114, 116, 118 and 120 provide ventricular pacing support as needed by the patient. Intrinsic atrial contractions sensed as P-waves and ventricular contractions sensed as R-waves by the pacemaker 160 (FIG. 2) reset the time intervals for pacing by the atrial channel 48 (FIG. 2) and the ventricular channel 50 (FIG. 2) respectively. In this example, during the atrial EP test the atrial channel 48 (FIG. 2) of the pacemaker 160 (FIG. 2) operates in AAI mode, with the time interval set to 400 ms or a programmed rate of 150 bpm. The ventricular channel 50 (FIG. 2) of the pacemaker 160.(FIG. 2) operates in VVI mode, with the time interval set to 1000 ms or a programmed rate of 60 bpm.

Figure 5:
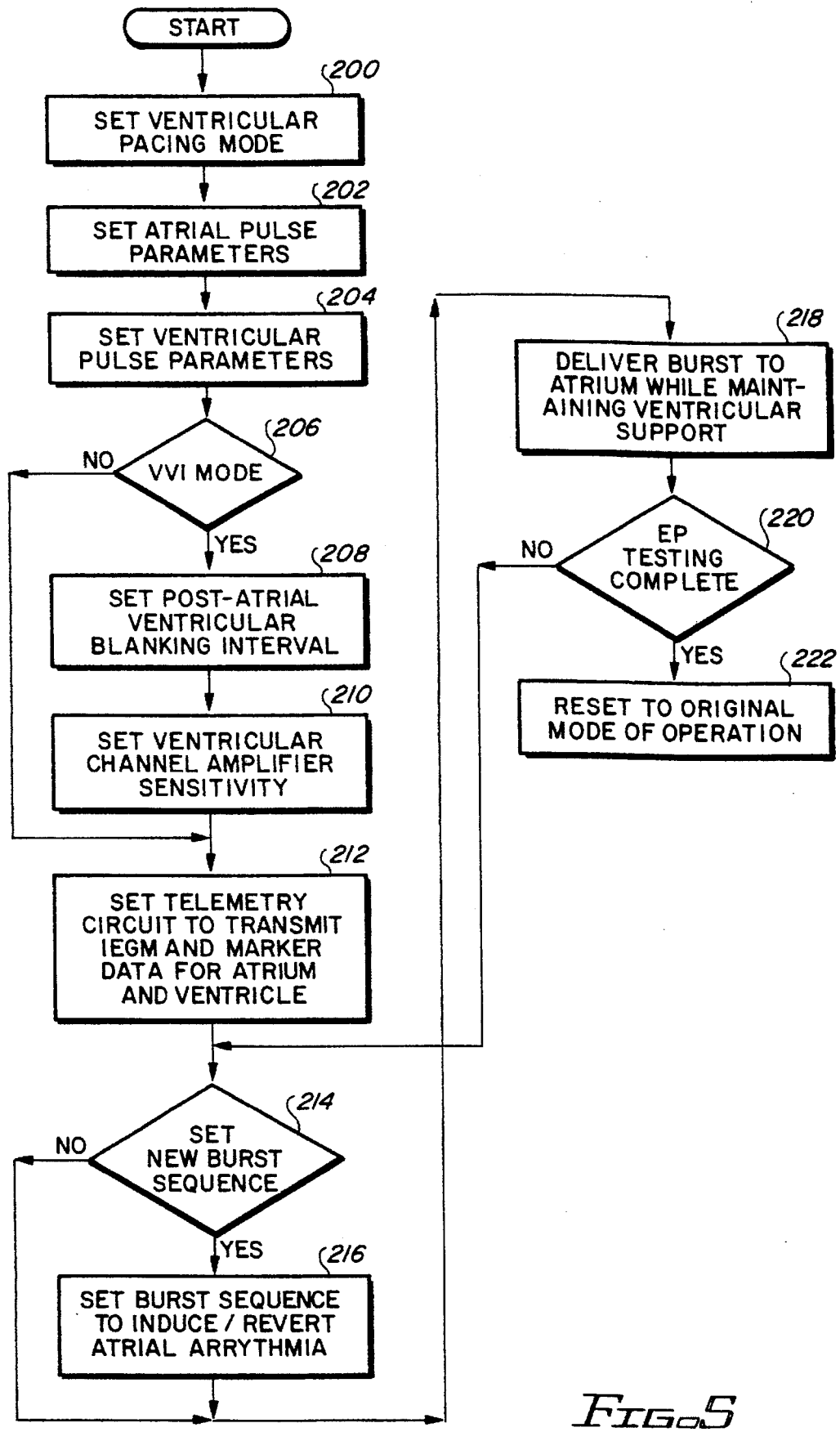
FIG. 5 is a logic flow diagram representing a control routine that may be used by the pacemaker of FIG. 2 to implement simultaneous atrial EP testing and ventricular pacing support in accordance with the principles of the present invention.

Referring now to FIG. 5, a logic flow diagram is described which represents a control routine performed by the control system 30 (FIG. 2) of the pacemaker 160 (FIG. 2) to implement atrial EP testing while maintaining ventricular pacing support in accordance with the principles of the present invention. The routine starts when the control system 52 (FIG. 2) receives a "start EP test" command from the programmer 140 (FIG. 3) through the telemetry circuit 68 (FIG. 2).

At step 200, the control system 52 (FIG. 2) sets the ventricular pacing mode to the mode selected by the physician using the programmer 140 (FIG. 3). Preferably, the ventricular pacing mode is set to VVI mode; however, VOO and VVT modes may be used instead. At step 202, the control system 52 (FIG. 2) sets the atrial pulse parameters by storing the parameters provided by the physician using the programmer 140 (FIG. 3) in the memory circuit 66 (FIG. 2). These parameters may include, for example, pulse width, pulse amplitude, blanking interval and amplifier sensitivity, among others. These parameters are used by the control system 52 (FIG. 2) to regulate the EP stimulation pulses generated by the atrial pulse generator 40 (FIG. 2) during EP testing.

At step 204, the control system 52 (FIG. 2) sets the ventricular pulse parameters by storing the parameters provided by the physician using the programmer 140 (FIG. 3) in the memory circuit 66 (FIG. 2). These parameters may include pulse width, pulse amplitude and pacing rate, among others. These perimeters are used by the control system 52 (FIG. 2) to regulate the pacing pulses generated by the ventricular pulse generator 42 (FIG. 2) while EP testing is being performed in the atrium. Advantageously, the ventricular pulse parameter used during atrial EP testing may differ from the atrial pulse parameters, and from the ventricular pulse parameters that are used when testing is not being performed by the pacemaker 160 (FIG. 2).

At test 206, the control system 52 (FIG. 2) determines if the physician has selected VVI mode at step 200. If VVI mode was selected, the control system 52 (FIG. 2) may receive an instruction to set a post-atrial ventricular blanking interval at step 208. The physician may choose to use this parameter to prevent sensing of atrial EP pulses by the ventricular channel sense amplifier 46 (FIG. 2). The duration of the blanking interval may be set by the physician based on the EP testing conditions and the condition of the patient. At step 210, the sensitivity of the ventricular channel sense amplifier 46 (FIG. 2) may be adjusted to reduce sensing of atrial EP pulses.

After step 210, or if VVI mode was not detected at test 206, the control system 52 (FIG. 2) sets the telemetry circuit 68 (FIG. 2) to transmit IEGM and marker data at step 212. Advantageously, the IEGM and marker data provide information identifying cardiac events in both the atrial chamber undergoing EP testing and the ventricular chamber that receives bradycardia pacing support during EP testing, as shown in (FIG. 4).

At test 214, the control system 214 (FIG. 2) determines if the physician has transmitted a new EP burst sequence using the programmer 140 (FIG. 2). If so, at step 216, the control system 52 (FIG. 2) stores the parameters that define the burst sequence in the memory circuit 66 (FIG. 2). The burst sequence stored in the memory circuit 66 (FIG. 2) may be a sequence that is known for either inducing or reverting an atrial arrhythmia. It should be noted that test 214 is not performed until a burst sequence has been stored in the memory circuit 66 (FIG. 2).

At step 218, the control system 52 (FIG. 2) causes the atrial channel 48 (FIG. 2) to administer the burst sequence defined at step 216 to the atrium in order to attempt to induce or revert an atrial arrhythmia. Simultaneously, the control system 52 (FIG. 2) causes the ventricular channel 50 (FIG. 2) to deliver bradycardia pacing pulses to the ventricle in the manner defined by the steps 200, 204, 208 and 210. Thus, atrial EP testing is performed while the patient continues to receive ventricular pacing support.

At test 220, the control system 52 (FIG. 2) determines if the physician, using the programmer 140 (FIG. 3) has indicated that EP testing is complete. If not, the control system 52 (FIG. 2) returns to test 214 to receive a new burst sequence, if the physician chooses to provide one. If testing is complete, step 222 is performed to return the pacemaker 160 (FIG. 2) to its original operating configuration. For example, the pacemaker 160 (FIG. 2) may resume conventional dual-chamber pacing. The pacing pacemakers that were being used prior to the start of EP testing are retained in the memory circuit 66 (FIG. 2) to allow the pacemaker 160 (FIG. 2) to return to its original mode of operation without requiring the physician to reenter those parameters.

Thus, a programmable pacemaker that can be used for noninvasive EP testing while maintaining ventricular support is provided, where the EP testing functions in one channel are decoupled from the underlying mode of operation of the other channel in the pacemaker. The implanted pacemaker can be used to perform serial EP studies. The pacemaker can induce and revert atrial arrhythmias by delivering bursts of stimulation pulses to the atrium in sequences that are defined by the physician. The pacemaker of the present invention can also provide ventricular pacing support operating in a single-chamber ventricular mode during atrial EP testing.

One skilled in the art will appreciate that the present invention can be practiced by other than the described embodiments, which are presented for purposes of illustration and not of limitation, and the present invention is limited only by the claims that follow.

What is claimed is:

1. An implantable cardiac stimulating device, comprising:
   means for performing electrophysiological testing in a first chamber of a heart;
   means for determining if said electrophysiological testing of the first chamber of the heart is being performed; and
   means for providing bradycardia pacing support in a second chamber of the heart while electrophysiological testing is being performed in the first chamber of the heart.

2. The implantable cardiac stimulating device of claim 1, wherein the performing means performs electrophysiological testing in an atrial chamber of the heart.

3. The implantable cardiac stimulating device of claim 1, wherein the providing means provides bradycardia pacing support in a ventricular chamber of the heart.

4. The implantable cardiac stimulating device of claim 1, wherein the providing means comprises means for providing demand pacing support.

5. The implantable cardiac stimulating device of claim 1, wherein the providing means comprises means for providing asynchronous pacing support.

6. The implantable cardiac stimulating device of claim 1, wherein the performing means comprises means for administering electrical stimulation to the first chamber of the heart to induce a cardiac arrhythmia.

7. The implantable cardiac stimulating device of claim 1, wherein the performing means comprises means for administering electrical stimulation to the first chamber of the heart to revert a cardiac arrhythmia.

8. The implantable cardiac stimulating device of claim 1, wherein:
   the performing means comprises means for administering electrical stimulation to the first chamber of the heart in accordance with a set of predetermined parameters having a first set of parameter values; and
   the providing means comprises means for administering electrical stimulation to the second chamber of the heart in accordance with a set of predetermined parameters having a second set of parameter values.

9. The implantable cardiac stimulating device of claim 8, wherein the first and second set of parameters are selected from the group consisting of pulse width, pulse amplitude, pacing rate, blanking interval and amplifier sensitivity.

10. The implantable cardiac stimulating device of claim 1 further comprising means for providing marker data for the first chamber and the second chamber of the heart.

11. An implantable dual-chamber pacemaker for performing electrophysiological testing in an atrial chamber of a patient's heart while maintaining ventricular pacing support, the pacemaker capable of telemetric communication with an external programmer, the pacemaker comprising:
   telemetry means for receiving commands from the external programmer;
   atrial pulse generating means for providing atrial stimulation pulses to an atrial chamber of the patient's heart;
   ventricular pulse generating means for providing ventricular stimulation pulses to a ventricular chamber of the patient's heart; and
   control means for causing the atrial pulse generating means to generate the atrial stimulation pulses in a sequence for performing electrophysiological testing in the atrial chamber and for causing the ventricular pulse generating means to generate the ventricular stimulation pulses to treat bradycardia in the ventricular chamber while the atrial stimulation pulses are being generated in a sequence for performing electrophysiological testing in the atrial chamber.

12. The pacemaker of claim 11, wherein the control means causes the atrial pulse generating means to generate the atrial stimulation pulses to treat bradycardia in the atrial chamber.

13. The pacemaker of claim 12, wherein the control means is coupled to the telemetry means such that the control means causes the atrial pulse generating means to generate the atrial stimulation pulses in a sequence for performing electrophysiological testing responsive to the telemetry means receiving the atrial electrophysiological testing command from the programmer.

14. The pacemaker of claim 13, wherein:
   the telemetry means receives an end of atrial electrophysiological testing command from the programmer; and
   the control means causes the atrial pulse generating means to generate the stimulation pulses to treat bradycardia in the atrial chamber responsive to the telemetry means receiving the end of atrial electrophysiological testing command.

15. The pacemaker of claim 14, wherein:
   the control means causes the ventricular pulse generating means to generate the ventricular stimulation pulses in accordance with a set of predetermined parameters, the parameters having a first set of values when the atrial pulse generating means is generating the atrial stimulation pulses in a sequence for performing electrophysiological testing; and
   the control means causes the ventricular pulse generating means to generate the ventricular stimulation pulses in accordance with the set of predetermined parameters, the parameters having a second set of values when the atrial pulse generating means is generating the atrial stimulation pulses to treat bradycardia.

16. The pacemaker of claim 11 further comprising ventricular sensing means coupled to the control means for sensing cardiac events in the ventricular chamber.

17. The pacemaker of claim 16, wherein the control means desensitizes the ventricular sensing means to atrial stimulation pulses generated by the atrial pulse generating means during electrophysiological testing.

18. The pacemaker of claim 17, wherein the control means provides a blanking signal, wherein the blanking signal when applied thereto, desensitizes the ventricular sensing means.

19. The pacemaker of claim 17, wherein the ventricular sensing means comprises amplifier means, and the control means desensitizes the ventricular sensing means by reducing the sensitivity of the amplifier means.

20. The pacemaker of claim 11, wherein the control means causes the ventricular pulse generating means to provide demand pacing support.

21. The pacemaker of claim 11, wherein the control means causes the ventricular pulse generating means to provide asynchronous pacing support.

22. The pacemaker of claim 11, wherein:
   the control means causes the atrial pulse generating means to generate the atrial stimulation pulses in accordance with a set of predetermined parameters, the parameters having a first set of values; and the control means causes the ventricular pulse generating means to generate the ventricular stimulation pulses in accordance with the set of predetermined parameters having a second set of values.

23. A method of performing noninvasive electrophysiological testing using an implantable cardiac stimulating device, comprising the steps of:

performing electrophysiological testing a first chamber of a heart using the implantable cardiac stimulating device; and providing bradycardia pacing in a second chamber of the heart using the implantable cardiac stimulating device while the step of electrophysiological testing proceeds in the first chamber of the heart.

24. The method of claim 23, wherein the performing step comprises performing electrophysiological testing in an atrial chamber of the heart.

25. The method of claim 23, wherein the providing step comprises providing bradycardia pacing support in a ventricular chamber of the heart.

26. The method claim 23, wherein the providing step comprises providing demand pacing support.

27. The method of claim 23, wherein the providing step comprises providing asynchronous pacing support.

28. The method of claim 23, wherein the performing step comprises administering electrical stimulation to the first chamber of the heart to induce a cardiac arrhythmia.

29. The method of claim 23, wherein the performing step comprises administering electrical stimulation to the first chamber of the heart to revert a cardiac arrhythmia.

30. The method of claim 23 wherein:

the performing step comprises administering electrical stimulation to the first chamber of the heart in accordance with a set of predetermined parameters, the parameters having a first set of values; and the providing step comprises administering electrical stimulation to the second chamber of the heart in accordance with the set of predetermined parameters, the parameters having a second set of values.

31. The method of claim 30, further comprising selecting the set of predetermined parameters from the group consisting of pulse width, pulse amplitude, pacing rate, blanking interval and amplifier sensitivity.

32. The method of claim 23 further comprising the step of providing marker data for the first chamber and the second chamber of the heart.

33. A method of using an implantable dual-chamber pacemaker for performing electrophysiological testing in an atrial chamber of a patient's heart while maintaining ventricular pacing support, the pacemaker having an atrial sense amplifier and a pulse generator and a ventricular sense amplifier and a ventricular pulse generator, the pacemaker in telemetric communication with an external programmer for receiving commands therefrom, comprising the steps of:

using the atrial pulse generator of the pacemaker to provide atrial stimulation pulses to an atrial chamber of the patient's heart;

using the ventricular pulse generator of the pacemaker to provide ventricular stimulation pulses to a ventricular chamber of the patient's heart;

controlling the atrial pulse generator to generate the atrial stimulation pulses in a sequence for performing electrophysiological testing in the atrial chamber; and controlling the ventricular pulse generator to generate the ventricular stimulation pulses to treat bradycardia in the ventricular chamber while the atrial stimulation pulses are being generated in a sequence for performing electrophysiological testing in the atrial chamber.

34. The method of claim 33 further comprising the step of controlling the atrial pulse generator to generate the atrial stimulation pulses to treat bradycardia in the atrial chamber.

35. The method of claim 34, further comprises receiving an atrial electrophysiological testing command from the programmer.

36. The method of claim 34, wherein the step of controlling the atrial pulse generator to generate the atrial stimulation pulses in a sequence for performing electrophysiological testing is performed responsive to receiving the atrial electrophysiological testing command.

37. The method of claim 36, further comprising the step of receiving an end of atrial electrophysiological testing command from the programmer; and the step of controlling the atrial pulse generator to generate the stimulation pulses to treat bradycardia in the atrial chamber is performed responsive to receiving the end of atrial electrophysiological testing command.

38. The method of claim 36, wherein the step of controlling the ventricular pulse generator to generate the ventricular stimulation pulses comprises:

controlling the ventricular pulse generator to generate the ventricular stimulation pulses in accordance with a predetermined set of pacing parameters, the parameters having a first set of values when the atrial pulse generator generates the atrial stimulation pulses in a sequence for performing electrophysiological testing; and controlling the ventricular pulse generator to generate the ventricular stimulation pulses in accordance with the predetermined set of pacing parameters, the parameters having a second set of values when the atrial pulse generator generates the atrial stimulation pulses to treat bradycardia.

39. The method of claim 33 further comprising the step using the ventricular sense amplifier to sense cardiac events in the ventricular chamber.

40. The method of claim 39 further comprising the step of desensitizing the ventricular sense amplifier to atrial stimulation pulses generated by the atrial pulse generator during electrophysiological testing.

41. The method of claim 40, wherein the desensitizing step comprises providing a blanking signal to the ventricular sense amplifier.

42. The method of claim 33, wherein the step of controlling the ventricular pulse generator comprises causing the ventricular pulse generator to provide demand pacing support.

43. The method of claim 33, wherein the step of controlling the ventricular pulse generator comprises causing the ventricular pulse generator to provide asynchronous pacing support.

44. The method of claim 33, wherein:

the step of controlling the atrial pulse generator comprises causing the atrial pulse generator to generate the atrial stimulation pulses in accordance with a predetermined set of parameters, the parameters having a first set of values; and the step of controlling the ventricular pulse generator comprises causing the ventricular pulse generator to generate the ventricular stimulation pulses in accordance with the predetermined set of parameters, the parameters having a second set of values.

* * * * *

US005653737C1

(12) EX PARTE REEXAMINATION CERTIFICATE (5082nd)
United States Patent
van Lake

(10) Number: US 5,653,737 C1
(45) Certificate Issued: Mar. 15, 2005

(54) PROGRAMMABLE PACEMAKER FOR NONINVASIVE EP TESTING FOR ATRIAL TACHYCARDIAS WITH VENTRICULAR SUPPORT

(75) Inventor: Paul van Lake, Scottsdale, AZ (US)

(73) Assignee: Pacesetter, Inc., Sylmar, CA (US)

Reexamination Request:
No. 90/006,671, Jun. 23, 2003

Reexamination Certificate for:
Patent No.: 5,653,737
Issued: Aug. 5, 1997
Appl. No.: 08/629,284
Filed: Apr. 8, 1996

(51) Int. Cl.$^7$ ............................................. A61N 1/362
(52) U.S. Cl. .............................. 607/9; 607/4; 128/697
(58) Field of Search .................................... 607/4, 9–28

(56) References Cited

U.S. PATENT DOCUMENTS

| | | | |
|---|---|---|---|
| 3,593,718 A | 7/1971 | Krasner et al. | 128/419 |
| 3,650,277 A | 3/1972 | Sjostrand et al. | 128/419 |
| 3,794,045 A | 2/1974 | Thaler | 128/419 |
| 4,009,721 A | 3/1977 | Alcidi | 128/419 |
| 4,049,003 A | 9/1977 | Walters et al. | 128/419 |
| 4,140,132 A | 2/1979 | Dahl | 128/419 |
| 4,169,480 A | 10/1979 | Digby et al. | 128/419 |
| 4,201,219 A | 5/1980 | Bozal Gonzalez | 128/419 |
| 4,237,897 A | 12/1980 | Beane et al. | 128/419 |
| 4,263,915 A | 4/1981 | McDonald et al. | 128/419 |
| 4,273,132 A | 6/1981 | Hartlaub et al. | 128/419 |
| 4,340,062 A | 7/1982 | Thompson et al. | 128/419 |
| 4,363,325 A | 12/1982 | Roline et al. | 128/419 |
| 4,365,633 A | 12/1982 | Loughman et al. | 128/419 |
| 4,390,020 A | 6/1983 | Herpers | 128/419 |
| 4,390,022 A | 6/1983 | Calfee et al. | 128/419 |
| 4,401,119 A | 8/1983 | Herpers | 128/419 |
| 4,404,972 A | 9/1983 | Gordon et al. | 128/419 |
| 4,428,378 A | 1/1984 | Anderson et al. | 128/419 |

(List continued on next page.)

FOREIGN PATENT DOCUMENTS

| | | | |
|---|---|---|---|
| EP | 0 015 779 A1 | 9/1980 | A61N/1/36 |
| EP | 0 049 812 A1 | 4/1982 | A61N/1/08 |
| EP | 0 077 800 B1 | 5/1982 | A61N/1/368 |
| EP | 0 064 002 A2 | 11/1982 | A61N/1/36 |
| EP | 0 077 844 A1 | 5/1983 | G06F/1/04 |
| EP | 0 077 845 A1 | 5/1983 | A61N/1/36 |
| EP | 0 089 014 A2 | 9/1983 | A61N/1/36 |
| EP | 0 107 483 A1 | 5/1984 | A61N/1/36 |
| EP | 0 114 679 A2 | 8/1984 | A61N/1/36 |
| EP | 0 140 472 A1 | 5/1985 | A61N/1/36 |
| EP | 0 160 801 A2 | 11/1985 | A61N/1/368 |
| EP | 0 201 990 A2 | 11/1986 | A61N/1/36 |
| EP | 0 216 725 A2 | 4/1987 | A61N/1/365 |
| GB | 2 153084 A | 8/1985 | A61B/5/04 |
| WO | WO 81/01659 | 6/1981 | A61N/1/36 |

OTHER PUBLICATIONS

"Advances In Dual–Chamber Pacing" (Intermedics Inc), Medical Electronics, No. 88, pp. 183–190 (Apr. 1986).

Advertisement for Diplos 04 Pacer from Biotronik; PACE, vol. 7, No. 3, Part I (May 1984).

(List continued on next page.)

*Primary Examiner*—Scott Getzow

(57) ABSTRACT

A programmable pacemaker that allows both noninvasive electrophysiological ("EP") testing for atrial tachycardias and ventricular pacing support, by allowing operation in the atrial channel to be decoupled from operation in the ventricular is provided. Many patients require EP testing to evaluate a predisposition to tachycardias. Many of these patients also have dual-chamber pacemakers for cardiac support. These systems can be noninvasively coupled to a external programmer enabling the already implanted system to serve as an in vivo EP laboratory. When performing noninvasive atrial EP testing with current dual-chamber pacemakers, the device must first be programmed to a single-chamber triggered mode. The present system allows the pacemaker to maintain ventricular pacing during EP testing.

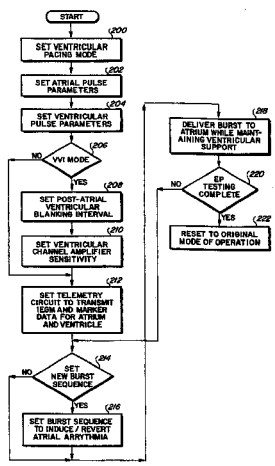

U.S. PATENT DOCUMENTS

| | | | |
|---|---|---|---|
| 4,429,697 A | 2/1984 | Nappholz et al. ............ | 128/419 |
| 4,436,092 A | 3/1984 | Cook et al. .................. | 128/419 |
| 4,467,807 A | 8/1984 | Bornzin ........................ | 128/419 |
| 4,485,818 A | 12/1984 | Leckrone et al. ............ | 128/419 |
| 4,503,857 A | 3/1985 | Boute et al. ................. | 128/419 |
| 4,527,568 A | 7/1985 | Rickards ...................... | 128/419 |
| 4,535,774 A | 8/1985 | Olson ........................... | 128/419 |
| 4,539,991 A | 9/1985 | Boute et al. ................. | 128/419 |
| 4,543,954 A | 10/1985 | Cook et al. .................. | 128/419 |
| 4,550,732 A | 11/1985 | Batty, Jr. et al. ............ | 128/419 |
| 4,567,892 A | 2/1986 | Plicchi et al. ............... | 128/419 |
| 4,576,183 A | 3/1986 | Plicchi et al. ............... | 128/723 |
| 4,585,004 A | 4/1986 | Brownlee ............. | 128/419 PT |
| 4,596,251 A | 6/1986 | Plicchi et al. ............... | 128/419 |
| 4,688,573 A | 8/1987 | Alt .............................. | 128/419 |
| 4,705,043 A | 11/1987 | Imran ................... | 128/419 PG |
| 4,712,555 A | 12/1987 | Thornander et al. ........ | 128/419 |
| 4,716,887 A | 1/1988 | Koning et al. ............... | 128/419 |
| 4,719,921 A | 1/1988 | Chirife ........................ | 128/419 |
| 4,730,618 A | 3/1988 | Lekholm et al. ............ | 128/419 |
| 4,776,338 A | 10/1988 | Lekholm et al. ............ | 128/419 |
| 4,779,618 A | 10/1988 | Mund et al. ................. | 128/419 |
| 4,802,483 A | 2/1989 | Lindgren .................... | 128/419 |
| 4,809,697 A | 3/1989 | Causey et al. .............. | 128/419 |
| 4,825,870 A | 5/1989 | Mann et al. .......... | 128/419 PG |
| 4,860,751 A | 8/1989 | Callaghan ................... | 128/419 |
| 4,870,968 A | 10/1989 | Wiertzfeld et al. ......... | 128/419 |
| 4,870,974 A | 10/1989 | Wang .......................... | 128/700 |
| 4,944,298 A | 7/1990 | Sholder ....................... | 128/419 |
| 4,967,746 A | 11/1990 | Vandegriff ............ | 128/419 PG |
| 4,974,589 A | 12/1990 | Sholder ................ | 128/419 PG |
| 5,123,412 A | 6/1992 | Betzold ....................... | 128/419 |
| 5,123,419 A | 6/1992 | Platt et al. ................... | 128/697 |
| 5,129,392 A | 7/1992 | Bardy et al. ............ | 128/419 D |
| 5,184,616 A | 2/1993 | Weiss .......................... | 128/419 |
| 5,282,836 A | 2/1994 | Kreyenhagen et al. ......... | 607/4 |
| 5,301,669 A | 4/1994 | Duncan .......................... | 607/9 |
| 5,312,447 A | 5/1994 | Begemann ..................... | 607/9 |
| 5,366,488 A | 11/1994 | Franberg et al. ............... | 607/9 |
| 5,388,586 A | 2/1995 | Lee et al. .................... | 128/704 |
| 5,507,783 A | 4/1996 | Buchanan ..................... | 607/14 |
| 5,514,164 A | 5/1996 | Mann et al. .................. | 607/25 |
| 5,522,857 A | 6/1996 | van Krieken ................... | 607/9 |
| 5,591,214 A | 1/1997 | Lu .................................. | 607/9 |
| 5,601,615 A | 2/1997 | Markowitz et al. ........... | 607/28 |
| 5,620,471 A | 4/1997 | Duncan ........................ | 607/14 |
| 5,776,167 A | 7/1998 | Levine et al. .................. | 607/9 |
| 5,788,717 A | 8/1998 | Mann et al. .................. | 607/14 |

OTHER PUBLICATIONS

Advertisement for COSMOS Pacing System from Intermedics, Inc.; PACE, vol. 7, No. 3, Part I (May 1984).

E. Alt, R. Volker, and A. Wirtzfeld, "Directly and Indirectly Measured Respiratory Parameters Compared with Oxygen Uptake and Heart Rate," PACE, vol. 8, Part II, No. 3, p. A–21 (May/Jun. 1985).

E. Alt, C. Hirgstetter, M. Heinz, "Central Venous Blood Temperature (CPT) for Control of Pacemker (PM) Rate," PACE, Vo. 8, No. 3, Part II, p. A–78 (May 1985).

E. Alt, H. Theres, M. Heinz, Ch. Hirgstetter, "Temperature Controlled Pacemaker Stimulation: First Clinical Results," German Journal of Cardiology, vol. 74, Supp. 5, p. 69 (Oct. 1985).

E. Alt, A. Wirtzfeld, "Physiological Pacing and Biological Rate Adjustment," Cardiac Pacemakers, pp. 87–99 (1985).

E. Alt, H. von Bibra, and H. Blomer, "Different Beneficial AV Intervals With DDD Pacing After Sensed Or Paced Atrial Events," Journal of Electrophysiology, vol. 1, No. 3, pp. 250–256 (1987).

E. Alt, "A Protocol for Treadmill and Bicycle Stress Testing Designed for Pacemaker Patients," Stimucoeur, vol. 15, No. 1, pp. 33–35 (1987).

E. Alt, M. Heinz, H. Theres, and M. Matula, "Function and Selection of Sensors for Optimum Rate–Modulated Pacing," New Pespectives in Cardiac Pacing, pp. 162–163, 176–183, 200–201.

J.Alzueta, I.Alvarez, C.Escudero, J.Moreu, A.Puente, J.L.Castillo–Olivares, and J. Marquez–Montes, "Bradycardia in an Experimental Model of Denervated Heart An Unusual Finding," PACE, vol. 10, Part II, p. 633 (May/Jun. 1987).

G. Amitzur, S. Rogel, and S. Samueloff, "The Modulating Effect of Thyroid Hormones on Ventricular Fibrillation Threshold in the Dog," PACE, vol. 10, Part II, p. 633 (May/Jun. 1987).

D.C. Amundson, M.B. Knudson, T.R. Hudrlik, D.J. MacCarter, A.W. Thornton, "A P–Wave Controlled Rate Responsive Algorithm," Cardiac Pacing, pp. 1239–1243 (1982).

K. Anderson, D. Humen, G. J. Klein, D. Brumwell, S. Huntley, "A Rate Variable Pacemaker Which Automatically Adjusts For Physical Activity," PACE, vol. 6, p. A–12, VII$^{th}$ World Symposium (May 1983).

G.E. Antonioli, G. Boriani, N. Bottoni, A. Capucci, G. Guardigli, M. Marconi, C. Menozzi, S. Sermasi, S. Silvani, T. Toselli, and G. Tumiotto, "Multicenter Study of Evaluation on DDDR vs DDD Pacing," Cardio Stimolazione, vol. 10, No. 3, p. 238 (Dec. 1992).

S.S. Barold, M.D. Falkoff, L. S. Ong, R. A. Heinle, "Characterization of Pacemaker Arrhythmias Due to Normally Functioning AV Demand (DVI) Pulse Generators," PACE, vol. 3, pp. 712–723 (Nov./Dec. 1980).

S.S. Barold, M.D. Falkoff, L.S. Ong, R.A. Heinle, "Interpretation Of Electrocardiograms Produced by a New Unipolar Multiprogrammable 'Committed' AV Sequential Demand (DVI) Pulse Generator," PACE, vol. 4, pp. 692–708; (Nov./Dec. 1981).

S.S. Barold, L.S. Ong,, M.D. Falkoff, R.A. Heinle, "Programmable Pacemakers—Clinical Indications, Compilations and Future Directions," The Third Decade of Cardiac Pacing, pp. 27–76 (1982).

S.S. Barold, M.D. Falkoff, L.S. Ong, R.A. Heinle, "Oversensing by Single–Chamber Pacemakers: Mechanisms, Diagnosis, and Treatment," Cardiology Clinics, pp. 565–585 (Nov. 1985).

S.S. Barold, P.H. Belott, "Behavior of the Ventricular Triggering Period of DDD Pacemakers," PACE, vol. 10, pp. 1237–1252 (Nov./Dec. 1987).

S.S. Barold, M.D. Falkoff, L.S. Ong, R.A. Heinle, "Upper Rate Response of DDD Pacemakers," New Perspectives in Cardiac Pacing, pp. 121–172 (1988).

R.L. Batey, D.A. Calabria, S. Shewmaker, M. Sweesy, "Crosstalk and Blanking Periods In a Dual Chamber (DDD) Pacemaker: A Case Report," Clin, Prog. Electrophysiol. and Pacing, vol. 3, No. 4, pp. 314–318 (1985).

D.G. Benditt, D. Dunbar, D. Woodrow Benson, Jr.; A. Dunningan, A. Almquist, M. Mianulli, J. Fetter, "Improved Exercise Capacity with a Rate–Responsive Pacemaker which Detects and Tracks Physical Activity," Abstracts of the 58$^{th}$ Scientific Sessions, p. III–433 (Nov. 1985).

T. Bennett, "Dynamic Characteristics of Alternative Physiological Pacing Modes"—Abstract, PACE, vol. 8, No. 2, p. 294 (Mar./Apr. 1985).

T.D. Bennett, W.H. Olson, G.A. Bornzin, M.D. Baudino, "Alternative Modes for Physiological Pacing," PACE, vol. 8, Part II, p. A–69 (May/Jun. 1985).

N.D. Berman, S.E. Dickson, B.M. Walker, I.H. Lipton, "Documenting the Value of Rate Hysteresis," Cardiac Pacing, pp. 597–599 (1982).

C. Bernheim, A. Markewitz, and R.M. Kemkes, "Can Reprogramming of Atrial Sensitivity Avoid an Endless Loop Tachycardia?" PACE, vol. 9, p. 293 (Mar./Apr. 1986).

M. Bilitch, R.S. Cosby, E.A. Cafferry, "Ventricular Fibrillation and Competitive Pacing," New England Journal of Medicine, vol. 276, No. 11, pp. 598–603 (Mar. 1967).

G. Boriani, A. Capucci, S. Specchia, M. Marinelli, A. Santarelli, M. Biffi, B. Magnani, "DDR Versus DDD Pacing: A Comparison by Means of Cardiopulmonary Exercise Test," Cardio Stimolazione, vol. 10, No. 3, p. 240 (Sep. 1992).

T. Bunge, D. Thompson, "Sensing Internal and External Body Activities," PACE, vol. 8, p. A–110, pp 786–701 (May/Jun. 1985, Part II).

C.L. Byrd, S.J. Schwartz, M. Gonzales, R.J. Ciraldo, W.Z. Yahr, M. Sivina, and J.J. Greenberg, "Rate Responsive Pacemakers and Cross Talk"—Abstract, PACE, vol. 11, p. 798 (Jun. Supplement 1988).

R.V. Calfee, P. Gordon, R.G. Baker, "Technical Advances in Cardiac Pacing—An Engineering Point of View," The Third Decade of Cardiac Pacing, pp. 471–477 (1982).

R. V. Calfee, "Dual–Chamber Committed Mode Pacing," PACE, vol. 6, pp. 367–391 (Mar./Apr. 1983, Part II).

L. Cammilli, L. Alcidi, G. Papeschi, "A New Pacemaker Autoregulating the Rate of Pacing In Relation to Metabolic Needs," Cardiac Pacing, pp. 414–419 (1977).

L. Cammilli, "The Autoregulating Pacemaker," Cardiac Pacing, pp. 1261–1262 (1982).

L. Cammilli, L. Alcidi, E. Shapland, S. Obino, "Results, Problems and Perspectives with the Autoregulating Pacemaker," PACE, vol. 6, pp. 488–493 (Mar./Apr. 1983, Part II).

B. Candelon, F. Wittkampf, and A. Diaz, "Technical Aspects of a Rate Responsive Pacemaker—The TX Pulse Generator," PACE, vol. 8, p. A–109 (May/Jun. 1985, Part II).

A. Castellanos, B.V. Berkovits, R. Fox, "QRS–Triggered Pacemaker and Arrhythmias Related to Early Systolic Stimulation," Annals of Cardiology, No. 4, pp. 485–490 (1971).

K. Chadda, B. Bloomfield, D. Harrington, R. Arbouet, J. Neglia, M. Bondenheimer, B. Berkovits, "Interruption of Spontaneous and Induced Tacharrhythmias by Scanning Self–Adapting Overdrive Pacing," Journal of the American College of Cardiology, vol. 9, No. 2, Supplement A, p. 141A (Feb. 1987).

W. M. Chardack, H. Ishikawa, F.J. Fochler, S. Souther, A.A. Gage, "Pacing and Ventricular Fibrillation," Annals New York Academy of Sciences, pp. 919–933 (1969).

G. Charos, C. Haffajee, B. Berkvits, R. Gold, A. Castellanos, J.S. Alpert, "An Effective and Potentially Superior Mode of Overdrive Pacing for Ventricular Tachycardia Interruption," PACE, vol. 8, p. 294; (Mar./Apr. 1985).

R.D. Fletcher, A. Cohen, A. Del Negro, M. Gomes, D.J. Cutler, S. Singh, R. DiBianco, "Patient Programming of Standard Implanted Pacemakers to Terminate Tachyarrhythmias," VIIth World Symposium, PACE, vol. 6, No. 3, Part II, p. A–138 (May 1983).

T. Cohen, "A Theoretical Right Atrial Pressure Feedback Heart Rate Control System to Restore Physiologic Control to the Rate–Limited Heart," PACE, vol. 7, pp. 671–677 (Jul./Aug. 1984).

W.J. Combs, D.W. Reynolds, A.D. Sharma, T.D. Bennett, "Cross–Talk in Bipolar Pacemakers," PACE, vol. 12, pp. 1613–1621 (Oct. 1989).

J.R. Cook, "Pacing Systems in The 80s," J. Louisiana State Medical Society, vol. 137, No. 4, pp. 40–50 (Apr. 1985).

M.J.E. Davis, G.C. Mews, G.D. Cope, "Initial Experience with Physiological Pacing," Aust. NZ. J. Med., vol. 15, pp. 246–251 (1985).

M. Davis, M. Pitney, C. May, "Automatic Mode Switching and Program Selection in a Rate Adaptive Dual Chamber Pacemaker," PACE, vol. 14, p. 664 (Apr. 1991, Part II).

O. de Divitiis, M. Santomauro, S. Fazio, M. Petitto, V. Liguori, B. Villari, C. Iaconon, S. Ferraro, M. Salvatore, "Cardiac Function in Patients with Breathing Frequency Controlled Pacemaker," PACE, vol. 8, p. A–9 (May/Jun. 1985, Part II).

M.J.L. de Jongste, E.J. van Binsbergen, J.H. Lahpor, I.I. Lie, "Early Experience with the Quintech 931 DDD Pacemaker," PACE, vol. 8, Part II, p. A–109 (May/Jun. 1985, Part II).

M.J.L. de Jongste, D. Nagelkarde, T. Ebels, and I.I. Lie, "Rate Adaptive Pacing Using the QT Interval," PACE, vol. 8, p. A–109, pp. 841–846 (May/Jun. 1985, Park II).

K. den Dulk, D. Richards, H.J.J. Wellens, M. Bertholet, J.C. Demoulin, A. Waleffe, H.E. Kulbertus, F.W. Lindemans, "A Versatile Pacemaker System with a Programmable Patient Activator for Termination of Tachycardias," PACE, vol. 6, No. 3, Part II, p. 508 (May 1983).

B.G. Denys, A.E. Aubert, H. Ector, and H. De Geest, "Intramyocardial Pressure at Various Pacing Rates," PACE, vol. 8, p. A–69 (May/Jun. 1985, Part II).

V. DiCola, J. Hawthorne, "Physiological Pacemakers," American Review of Medicine, vol. 35, 493–502 (1984).

R.M. Donaldson, K. Fox, A.F. Rickards, "Initial Experience with A Physiological, Rate Responsive Pacemaker," British Medical Journal, vol. 286, ppl. 667–671 (Feb. 1983).

R.M. Donaldson, A.F. Rickards, "A Microprocessor Based Algorithm Controlled Antiarrhythmic and Rate–Responsive Pacemaker," Computers in Cardiology, $10^{th}$ Annual Meeting, pp. 353–355 (Oct. 1983).

R.M. Donaldson, A.F. Rickards, "Rate Responsive Pacing Using the Evoked QT Principle. A Physiological Alternative to Atrial Synchronous Pacemakers," PACE, vol. 6, pp. 1344–1349 (Nov./Dec. 1983).

R.M. Donaldson, A.F. Rickards, "Towards Multisensor Pacing," American Heart Journal, vol. 106, No. 6, pp. 1454–1457 (Dec. 1983).

D. Escher, "Pacemakers of The 1980's," Medical Instrumentation, vol. 18, No. 1, pp. 29–34 (Jan./Feb. 1984).

S. Faerestrand, O.J. Ohm, "A Longitudinal Study of the Hemodynamic Benefit of Atrio–Ventricular Snychronous Pacing Evaluated by Doppler Echocardiography," PACE, vol. 8, p. A–9, (May/Jun. 1985, Part II).

L. Fananapazir, M. Rademaker, D. Bennett, "Performance of the TX Pacemaker," PACE 8, p. A–110 (May/Jun. 1985, Part II).

L. Fananapazir, M. Rademaker, D.H. Bennett, "Reliability of the Evoked Response In Determining the Paced Ventricular Rate and Performance of the QT or Rate Responsive (TX) Pacemake," PACE, vol. 8, pp. 701–714 (Sep./Oct. 1985).

N.E. Fearnot, L.A. Geddes, H.J. Smith, "Principles of Exercise Responsive Pacemakers," Engineering in Medicine & Biology, pp. 25–29 (Jun. 1984).

N. Fearnot, D. Jolgren, W. Tacker, L. Geddes, "Exercise Responsive Pacing Using RV Blood Temperature," 37th Acemb, p. 216 (Sep. 1984).

N.E. Fearnot, D. L. Jolgren, W.A. Tacker, J.P. Nelson, L.A. Geddes, "Increasing Cardiac Rate by Measurement of Right Ventricular Temperature," PACE, vol. 7, pp. 1240–1245 (Nov./Dec. 1984, Part II).

N.E. Fearnot, D.L. Jolgren, T.D. Sellers, "Pacemaker Update: Temperature," Research Digest Condensed Version, vol. 1, No. 1; pp. 1–9 (1985).

G.A. Feruglio, A.F. Rickards, K. Steinbach, B.S. Goldman, V. Parsonnet, A. Dussault, "Pacing in the World Today," VIIth World Symposium, PACE, vol. 6, P. A–149 (May 1983).

J.D. Fisher, G. Katz, S. Furman, I. Rubin, "Differential Response to Carotid Sinus Massage in Cardiac Patients With and Without Syncope," PACE, vol. 4, p. A–11 (May/Jun. 1981).

J.D. Fisher, S.G. Kim, E. Ostrow, "Ultra–Rapid Single Capture Train Sti ulation for Termination of Ventricular Tachycardia," PACE, vol. 4, p. A–11 (May/Jun. 1981).

R.D. Fletcher, A. Cohen, R. Cohen, A. Del Negro, D.J. Cutler, J.G. Keimel, "SErial Noninvasive Electropysiologic Testing Using Implanted Single And Dual Chamber Pacemakers," VIIth World Symposium PACE, vol. 6, No. 3, Part II, p. 563 (May 1983).

R.D. Fletcher, J. Keimel, L. Larca, J. Cox, A. Del Negro, R. Di Bianco, S. Singh, "Non–invasive Serial Electrophysiologic Testing Using an Implanted Pacemaker to Track Chest Wall Stimuli," The American Journal of Cardiology, vol. 47, p. 392 (Feb. 1981).

R.D. Fletcher, A.I. Cohen, A. Del Negro, "Noninvasive Electrophysiologic Studies Using Implanted Pacemakers," Modern Cardiac Pacing, pp. 421–438 (May/Jun. 1985).

R.D. Fletcher, J.G. Keimel, L. Larca, J.A. Cox, A. Del Negro, R. Di Bianco, S. Singh, "Noninvasive Serial Electrophysiologic Testing Using an Implanted Pacemaker," PACE, vol. 4, p. A–11 (May–Jun. 1981).

R. Fletcher, J. Keimel, A. Cohen, R. Cohen, A. Del Negro, D.J. Cutler, "Synchronized Programming—A New Technique for Serial Noninvasive Electrophysiological Testing in Single and Dual Chamber Implanted Pacemakers," J. Am. Coll. Cardiol., vol. 1, No. 2, p. 720 (1983).

R. Fletcher, A. Cohen, R. Cohen, B. Lee, D.J. Cutler, A. Del Negro, S. Singh, R. DiBianco; "Efficacy Of Noninvasive Electrophysiological Testing in Patients with Implanted Pacemakers To Control Arrhythmia," J. Am. Cardiol., vol. 3, No. 2, p. 538 (Feb. 1984).

R.D. Fletcher, A.I. Cohen, D. Joshua, A.A. Del Negro, B.I. Lee, J.S. Gottdiener, S.N. Singh, "Dual Chamber Pacemakers as Implanted Electrophysiology Laboratories," Circulation, vol. 70, No. 4, p. II–201 (Oct. 1984).

R. Flink, "Future Directions of Cardiac Pacemaker Research—A Survey," Medical Instrumentation, vol. 18, No. 1, pp. 25–28 (Feb. 1984).

G. Fontaine, R. Frank, J.C. Petitot, J. Vedel, F. Fillette, R. Dzietham, Y. Grosgogeat, "The Risks of Programmability," The Third Decade of Cardiac Pacing, pp. 77–103 (1982).

J. A. Franciosa, C.L. Leddy, M. Wolen, D.E. Schwartz, "Relation Between Hemodynamic and Ventilatory Responses in Determining Exercise Capacity in Severe Congestive Heart Failure," Am J. Cardiol., vol. 53, pp. 127–134 (1984).

W.J. Franch; J.J. Florio, "Mode Change During DDD/Rate Responsive Pacing: Technical Benefits & Physiologic Results," PACE, vol. 11, p. 798 (June Supplement 1988).

W.J. Franch, R.J. Haskell, G.W. Wesley, J. Florio, "Physiological Benefits of a Pacemaker with Dual Chamber Pacing at Low Heart Rates and Single Chamber Rate Responsive Pacing During Exercise," PACE, vol. 11, pp. 1840–1845 (Nov. 1988, Part II).

H.D. Friedberg, S.S. Barold, "On Hysteresis In Pacing," J. Electrocardiology, vol. 6, No. 1, pp. 1–2 (1973).

H.D. Funke, "Ein Herschrittmacher Mit Belastungsabhangiger Frequenzregulation (A Cardiac Pacemaker With Activity–Dependent Frequency Regulation)," Biomedizinische Technik, vol. 20, No. 6, pp. 225–228 (1975).

H.D. Funke, "Cardiac Pacing with Universal DDD Pulse Generator: Technology and Electrophysiological Considerations" The Third Decade of Cardiac Pacing, pp. 191–223 (1982).

S. Furman, H. Reicher–Reiss, D.J.W. Escher, "Atrioventricular Sequential Pacing and Pacemakers," CHEST, vol. 63, No. 5, pp. 783–789 (May 1973).

S. Furman, "Dual Chamber Pacemakers: Upper Rate Behavior," PACE, vol. 8, pp. 197–214 (Mar./Apr. 1985).

S. Furman, "Pacemaker Sensing," PACE, vol. 9, p. 157 (Mar./Apr. 1996).

S. Furman, "Basic Concepts" A Practice of Cardiac Pacing, p. 27–73 (1986).

S. Furman, "Comprehension of Pacemaker Timing Cycles" A Practice of Cardiac Pacing, pp. 159–217 (1986).

M.D. Gabry, P. Klementowicz, S. Furman, "Balanced Endless Loop Tachycardia," PACE, vol. 9 (Mar./Apr. 1986).

D. Gascon, F. Errazquin, J. Nieto, J. Burgos, A. Diaz, B. Candelon, L. Castillion, "Preliminary Clinical Evaluation of a New DDDM Pacemaker (Quintech DDD931)," PACE, vol. 8, Part II, p. A–78 (May/Jun. 1985).

L.A. Geddes, N.E. Fearnot, H.J. Smith, "The Exercise–Responsive Cardiac Pacemaker," IEEE Transactions on Biomedical Engineering, vol. BME–31, No. 12, pp. 763–770 (Dec. 1984).

L.A. Geddes, "Control Methods for Pacemakers," p. 24.

P. Gillette, "Critical Analysis of Sensors for Physiological Responsive Pacing," PACE, vol. 7, pp. 1263–1266, (Nov./Dec. 1984, Part II).

A. Goicolea de Oro, M.W. Ayza, R. de la Llana, J.A. Morales, J.R. Gutierrez Diez, J. Gonzalez Alvarez, "Rate–Responsive Pacing: Clinical Experience," PACE, vol. 8, p. 322–28 (May/Jun. 1985, Part I).

A., Goicolea de Oro, J.G. Lorenzo, J. Rodriguez, I. Terol, R. Coma, M. Wilhelmi, A. Diaz, "Rate Responsive Multiprogrammable Pacemaker Controlled by QT Interval, Our Experience in 31 Cases," PACE, vol. 8, p. A–109 (May/Jun. 1985, Part II).

J.C. Griffin, A.P. Nielsen, W.L. Finke, J.W. Clark, "A New Method of Rhythm Identification: Endocardial Electrogram Morphology," Circulation, Part II, vol. 70, No. 4, p. 201 (Oct. 1984).

J. C. Griffin, "Central Venous Temperature: An Indicator of Exercise," Department of Medicine and Cardiovascular Research Institute, University of California, San Francisco, Calif.; pp. 792–797.

R. Haberl, E. Hengstenberg, G. Steinbeck, "Single Beat Analysis of Frequency Content in the Surface ECG for Identification of Patients with Ventricular Tachycardia," Abstracts of the 58th Scientific Sessions, p. III–433 (Nov. 1985).

C.I. Haffajee, J.C. Love, J.S. Alpert, "Is Pacemaker Mediated Tachycardia with DDD Pacemakers Obsolete? Follow–up Study on 81 Patients," PACE, vol. 7, p. 470 (May/Jun. 1984, Part I).

J.W. Harthorne, "The Future of Cardiac Pacing," Modern Cardiac Pacing, Ch. 43, pp. 949–958 (1985).

M.H. Hamersma, K.A. da Raad, P.C. van der Linden, "Sensor Driving Pacemakers: Indications for Rate Responsive Pacing," PACE, vol. 8, p. A–21 (May/Jun. 1985, Part II).

R.J. Haskell, W.J. French, "Rate Responsiveness or Atrial Augmentation as Most Important Physiological Factor in Enhanced Exercise Performance in Patients with Dual Chamber Pacemakers," JACC, vol. 9, No. 2, p. 141A (Feb. 1987).

R.G. Hauser, "The Electrocardiography of AV Universal DDD Pacemakers," PACE, vol. 6, pp. 399–409 (Mar./Apr. 1983, Part II).

R.G. Hauser, "Techniques for Improving Cardiac Performance with Implantable Devices," PACE, vol. 7, pp. 1234–1239 (Nov./Dec. 1984, Part II).

D. Hayes, D. Holmes, J. Gray, J. Fetter, G. Aram, P. Tarjan, L. Prechter, "The Effects of Nuclear Magnetic Resonance on Implantable Pulse Generators," PACE, vol. 9, p. 293 (Mar./Apr. 1986).

D.L. Hayes, "Pacemaker Electrocardiographyy," A Practice of Cardiac Pacing, pp. 305–331 (1986).

D.L. Hayes, S.T. Higano, G. Elsinger, "Utility of Rate Histograms in Programming and Follow–Up of a DDDR Pacemaker," Mayo Clin. Proc., vol. 64, pp. 495–502 (May 1989).

A. Hedman, R. Nordlander, K. Pehrsson, "QT and Q–AT Intervals of Paced Complexes at Different Rates and Modes of Pacing," Division of Cardiology, Department of Medicine, Karolinska Hospital, Stockholm, Sweden, pp. 853–856.

J.M. Herre, J.C. Griffin, T.D. Schuenemeyer, J.C. Luck, D.E. Mann, S. Magro, G.W. Lawrie, A.P. Nielsen, C.R.C. Wndham, "Diagnostic and Therapeutic Use of Permanent Triggered Pacemakers in Ventricular Tachycardia," VIIth World Symposium, PACE, vol. 6, No. 3, Part II, p. A–138 (May 1983).

G. Hindricks, W. Haverkamp, U. Rissel, H. Gulker, "Feasibility of NDYAG–Laser Photoablation for the Non–Pharmacological Treatment of Ventricular Tachyarrhythmias," PACE, vol. 10, Part II, p. 688 (May/Jun. 1987).

G. Hindricks, W. Haverkamp, L. Dreismann, J. Vogt, H. Gulker; "Electrophysiological and Antiarrythmic Efficacy of the New Propafenon–Derivate Hydroxyfenone," PACE, vol. 10, Part II, p. 688 (May/Jun. 1987).

E. Hoffman, T.H. von–Arnim, G. Steinbeck, "Transcutaneous Cardiac Pacing During Cardiopulmonary Resuscitation (CPR)," PACE, vol. 10, Part II, p. 688 (May/Jun. 1987).

L.K. Holley, D.L. Ross, K.J. Palmer, B. Ho, A.R. Dennis, J.B. Uther, "Analysis of Pacing Modalities for Ventricular Tachycardia Termination,", PACE, vol. 8, p. 294 (Mar./Apr. 1985).

W.J. Hollins, R.B. Leman, J.M. Kratz, P.C. Gillette, "Limitations of the Long–Term Clinical Application of Rate Hysteresis," PACE, vol. 10, pp. 302–304 (Mar./Apr. 1987).

D.R. Holmes, "Pacing for Tachycardia," A Practice of Cardiac Pacing, pp. 413–431 (1986).

J. Horgan, "Medical Electronics," IEEE Spectrum, pp. 89–94 (Jan. 1985).

E. Horstmann, "Brief Exercise and Double Sensor Pacing Based on QT Interval and Activity. Early Results with the Topaz," Cardio Stimolazione, vol. 10, No. 3, p. 239 (Sep. 1992).

D.P. Humen, K. Anderson, D. Brumwell, S. Huntley, G.J. Klein, "A Pacemaker which Automatically Increases its Rate with Physical Activity," Cardiac Pacing, pp. 259–264 (May 1983).

D. Humen, W.J. Kostuk, G.J. Klein, "Activity–Sensed Rate Responsive Pacing: Treadmill Performance and Hemodynamic Characteristics," JACC, vol. 3, No. 2, p. 508 (Feb. 1984).

D.P. Humen, W.J. Kostuk, G.J. Klein, "Activity–Sensing, Rate–Responsive Pacing: Improvement in Myocardial Performance with Exercise," PACE, vol. 8, pp. 52–59 (Jan./Feb. 1985).

W. Irnich, Letter to the Editor Re: Definition of Negative and Positive Hysteresis, PACE, vol. 5, pp. 283–285 (Mar./Apr. 1982).

W. Irnich, "Interference in Pacemakers," PACE, vol. 7, pp. 1021–1048 (Nov./Dec. 1984, Part I).

D.L. Janosik, A.C. Pearson, T.A. Buckingham, A.J. Labovitz, R.M. Redd, D. Mrosek, "The Hemodynamic Benefit of Differential Atrioventricular Delay Intervals for Sensed and Paced Atrial Events During Physiologic Pacing," JACC, vol. 14, No. 2, pp. 499–507 (Aug. 1989).

D. Jolgren, N. Fearnot, L. Geddes, "A Rate Responsive Pacemaker Controlled by Riight Ventricular Blood Temperature," J. Am. Coll. Cardiol., vol. 1, No. 2, p. 720 (1983).

D. Jolgren, N. Fearnot, L. Geddes; A Rate–Responsive Pacemaker Controlled by Right Ventricular Blood Temperature; PACE, vol. 7, pp. 794–801 (Sep./Oct. 1984, Part V).

B.A. Jones, R.E. Patterson, S.E. Epstein, "Electrical Instability as a Function of Myocardial Infarction Size," The American Journal of Cardiology, vol. 47, p. 392 (Feb. 1981).

W. Jung, M. Manz, B. Lüderitz, "Welche Programmierbaren Leistungen Der Aggregate sind Verfügbar, und wie ist ihre Klinische Relevanz?" Herz, vol. 16, No. 3, pp. 158–170 (Jun. 1991).

I. Karlöf, "Haemodynamic Effect of Atrial Triggered versus Fixed Rate Pacing at Rest and During Exercise in Complete Heart Block," Acta Med. Scand., vol. 197, pp. 195–206 (1975).

R.A. Kenny, A. Ingram, T. Mitsuoka, K. Walsh, R. Sutton, "Optimal Pacing Mode for Angina Pectoris Patent," PACE, vol. 8, p. 781 (Sep./Oct. 1985).

R.A. Kenny, A. Ingram, T. Mitsuoka, K. Walsh, R. Sutton, "Comparison of Sensor Driven Physiological Pacing Systems," PACE, vol. 8, No. 5, p. 781 (Sep./Oct. 1985).

I.E. Kersschot, P. Ortmanns, M.A. Goethals, "Atrial Pacing Bigeminy: A Manifestation of Crosstalk," PACE, vol. 8, pp. 402–407 (May/Jun. 1985, Part I).

P.J. Kertes, C.J. Hilton, E.J. Jones, P.F. Walter, R.W.F. Campbell, "Surgical Management of Early Post–Infarction, Drug Resistant Ventricular Tachyarrhythmias," PACE, vol. 8, p. 781 (Sep./Oct. 1985).

P.J. Kertes, S.J. Pollack, P.F. Walter, "Programmed Stimulation for Ventricular Tachycardia: Responses Predicted by Signal Averaging in Patients with and without Coronary Disease," Abstracts of the 58$^{th}$ Scientific Sessions, p. III–433 (Nov. 1985).

F. Klementowicz, R. Steingart, S. Furman, "Atrial Contribution to Left Ventricular Volume Assessed by Ventriculography," PACE, vol. 8, p. A–9 (May/Jun. 1985, Part II).

M.B. Knudson, D. Amundson, A. Thornton, J. Shapland, M. Mosharrafa, "Hemodynamic Demands—Are They Met By A Rate Responsive Physiologic Pacemaker?" PACE, vol. 4, p. A–53 (May/Jun. 1981).

M.B. Knudson, D.C. Amundson, M. Mosharrafa, "Hemodynamic Demand Pacing," The Third Decade of Cardiac Pacing, pp. 249–264 (1982).

W.H. Ko, "A Review of Implantable Sensors," PACE, vol. 6, pp. 482–487 (Mar./Apr. 1983).

Y. Koretsune, K. Kodama, M. Inoue, S. Nanto, K. Taniura, M. Hori, M. Mishima, H. Abe, "Disadvantageous Effects of Ventricular Pacing on Cardiac Function and Myocardial Energetics," JACC, vol. 3, No. 2, p. 507 (Feb. 1984).

B.E. Kristensson, K. Arnman, P. Smedgard, L. Ryden, "Physiological Versus Single–Rate Ventricular Pacing: A Double–Blind Cross–Over Study," PACE, vol. 8, pp. 73–84 (Jan./Feb. 1985).

K. Kubisch, W. Peters, I. Chiladakis, H. Greve, H. Heuer, "Clinical Experience with the Rate Responsive Pacemaker Sensolog 703," PACE, vol. 11, pp. 1829–1833 (Nov. 1988, Part II).

A. Laczkovics, M. Schilck, U. Losert, G. Simbrunner, "The Use of Central Venous Blood Temperature (CVT) as a Guide for Rate Control in Pacemaker–Therapy," VIIth World Symposium, PACE, vol. 6, p. A–12 (May 1983).

M.S. Lampadius; Event–Triggered Rheographic Ventilation Sensor for Pacemaker Rate Control; PACE, vol. 8, Part II(May/Jun. 1985).

C.P. Lau, W.S. Tse, A.J. Camm, "Clinical Experience with Sensolog 703: A New Activity Sensing Rate Responsive Pacemaker," PACE, vol. 11, pp. 1444–1455 (Oct. 1988).

M.E. Leckrone, V.T. Cutolo, D. Ennen, E. Zayas, P. P. Tarjan, "A Microprocessor–Based, Two–Chamber Physiologic Pacemaker," The Third Decade of Cardiac Pacing—Advances in Technology and Clinical Applications, pp. 167–189 (1982).

L. Lemberg, A. Castellanos, A.G. Arcebal, B.V. Berkovits, O. Hernandez–Pierretti, "Systolic and Diastolic Pacemaker Induced Repetitive Firing in the Human Heart," Journal of Electrocardiology, pp. 353–362 (1969).

P.A. Levine, "Normal and Abnormal Rhythms Associated with Dual–Chamber Pacemakers," Cardiology Clinic, vol. 3, No. 4, pp. 595–616 (Nov. 1985).

P.A. Levine, B.S. Lindenberg, "Upper Rate Limit Circuit–Induced Rate Slowing," PACE, vol. 10, pp. 310–314 (Mar./Apr. 1987).

P.A. Levine, F.J. Venditti, P.J. Podrid, M.D. Klein, "Therapeutic and Diagonostic Benefits of Intentional Crosstalk Mediated Ventricular Output Inhibition," PACE, vol. 11, pp. 1194–1201 (Aug. 1988).

P.A. Levine, R.C. Mace, "Normal Rhythms Associated with Atrioventricular Sequential (DVI) Pacing," Pacing Therapy: A Guide to Cardiac Pacing for Optimum Hemodynamic Benefit, Ch. 13, pp. 191–201 (1983).

P.A. Levine, R.C. Mace, "Assessment and Management of Cross–Talk," Pacing Therapy: A Guide to Cardiac Pacing for Optimum Hemodynamic Benefit, Ch. 13, pp. 239–251 (1983).

P.A. Levine; J.P. Selzer, "Fusion, Pseudofusion, Pseudo–Pseudofusion and Confusion: Normal Rhythms Associated with Atrioventricular Sequential "DVI" Pacing," Clinical Progress in Pacing and Electrophysiology, vol. 1, No. 1, pp. 70–80 (1983).

B.D. Lindsay, S.T. Rothbart, N. Wasty, D. Pantopoulos, S. Saksena, "Prospective Evaluation of Ventricular Pacing and High Energy Transvenous Shocks Using a Triple Electrode Array for Cardioversion of Ventricular Tachycardia," Journal of the American College of Cardiology, vol. 9, No. 2, Spplement A, p. 141A (Feb. 1987).

J.W. Lister, P.P. Tarjan, "The Implantable Electrophysiology Laboratory," Modern Cardiac Pacing, Ch. 43, pp. 759–772 (1985).

A. Lopman, C.L. Langer, S. Furman, D.J.W. Escher, "A Fifteen Year Comparative Study of Cardiac Pacing Costs," The American Journal of Cardiology, vol. 47, p. 392 (Feb. 1981).

B. Lozada, A. Dussaut, H. Mazzetti, M.C. Tenrori, "Chronic Thresholds and Strength—Duration Curve in Chagas Disease," PACE, vol. 8, p. A–110 (May/Jun. 1985, Part II).

R.M. Luceri, A.V. Ramierz, A. Castellanos, L. Zaman, R.J. Thurer, R.J. Myerburg, "Ventricular Tachycardia Produced by a Normally Functioning AV Sequential Demand (DVI) Pacemaker With 'Committed' Ventricular Stimulation," JACC, vol. I, No. 4, pp. 1177–1179 (1983).

P. Mabo, C. Varin, C. Vauthier, C. De Place, F. Paillard, C. Dauber (Univ. Hospital, Rennes, France), "Deleterious Hemodynamic Consequences of Isolated Long PR Intervals: Correction by DDD Pacing," Cardiac Pacing/Exercise Testing, p. 225.

B. Maisch, H. Steilner, "Rate Responsive Pacing—Initial Experience with The QT (TX/Quintech) and Biorate Pacemakers," Cardiac Pacemakers (Darmstadt: Steinkopff Verlag) p. 100–106 (1985).

S. Mangiameli, A. Circo, G. Doris, B. Aloisi–Bajunco, M. Abbate, L. Carli, B. Brancati, A. Stuto, N. Digiovanni, G. Bellanca, "Clinical Evaluation Report Topaz: First Dual Sensor Pacemaker," Cardio Stimolazione, vol. 10, No. 3, p. 239 (Sep. 1992).

F.E. Marchlinkski, M. Cain, R.A. Falcone, J.F. Spear, M.E. Josephson, "Changes in Ventricular Refractoriness Following a Premature Stimulus: Implications for Tachycardia Induction," VIIth World Symposium, PACE, vol. 6, No. 3, Part II, p. 509 (May 1983).

A. Markewitz, C. Bernheim, B.M. Kemkes, "Clinical Concerns of the Blanking Period," PACE, vol. 9, p. 293 (Mar./Apr. 1986).

A. Markewitz, K. Wenke, C. Weinhold, "Deterioration of AV Conduction in AAIR Patients: Can it be Predicted Intraoperatively?" PACE, vol. 13, p. 1203 (Sep. 1990).

P. McElroy, K.T. Weber, T.A. Nappholz, "Heart Rate, Ventilation, Mixed Venous Temperature, pH and Oxygen Saturation During Incremental Upright Exercise," PACE, vol. 8, p. 784 (Sep. 1985).

P.A. McElroy, K.T. Weber, J.S. Janicki, T.A. Nappholz, "Mixed Venous Temperature, pH and Oxygen Saturation and Heart Rate During Exercse," Circulation, vol. 72, Suppl. III, p. 1727 (1985).

E.L. Michelson, M. Naito, D. David, E.N. Moore, L.S. Dreifus, "Meobentine Sulfate: Antiarrhythmic Efficacy and Mechanism of Action in a Chronic Canine Model of Myocardial Infarction Susceptible to Ventricular Tachyarrhythmias," American Journal of Cardiology, vol. 47, p. 392; (Feb. 1981).

D. Morse, "What's Wrong with Pacing?" PACE, vol. 5, pp. 455–456 (May/Jun. 1982).

J. Mugica, M. Mosharrafa, J.P. Letouzey, J.Y. Jacquet, D. MacCarter, M.B. Knudson, "Hemodynamic Demand Pacing: Study of Five Cases," Cardiac Pacing, pp. 1105–1106 (1982).

J. Mugica, S.S. Berold, A. Ripart, "The Smart Pacemaker," New Perspectives in Cardiac Pacing.2, Ch. 23, pp. 545–577 (Sep. 1991).

A.P. Nielsen, J.C. Griffin, W. L. Finke, "Evaluation of Temperature and $O_2$ Saturation during Treadmill Exercise in Older Men: Possible Indices for a Sensor Driven Pacemaker System," JACC, vol. 5, No. 2, p. 393 (1985).

G. Neumann, F. Camerini, "Sick Sinus Syndrome: Long–Term Results With Atrial and Ventricular Pacing," Cardiac Pacing, pp. 989–995 (1982).

R. Nordlander, A. Hedman, K. Pehrsson, H. Astrom, "Clinical Experience With Rate Responsive Pacing by the Evoked QT," PACE, vol. 8, p. A–110 (May/Jun. 1985, Part II).

A. Osterspey, H.W. Hopp, V. Hombach, H.J. Deutsch, D.W. Benrenbeck, M. Tauchert, H.H. Hilger, "Diagnostic and Prognostic Significance of Ventricular Late Potentials (VLP) in Patients with Coronary Heart Disease (CHD)," VIIth World Symposium, PACE, vol. 6, No. 3, Part II, p. 561 (May 1983).

G. Palma, F. de Bellis, A. Solinas, M. Falcone, A. Ciccaglioni, A. Venerando, A. Reale, "Sensor–Free Physiological Pacing," PACE, vol. 8, Part II, p. A–21 (May/Jun. 1985).

V.J. Paolone, R. Burian, S. Rosinsky, A.M. Paolone, "Evaluation of the Metabolic Cost of the Three Levels of Exercise Prescribed for Parcourse Stations," Proc. $8^{th}$ Annual Mid–Atlantic Meeting of the American College of Sports Medicine Pennsylvania State University (Feb. 1985).

V. Parsonnet, A.D. Bernstein, "Cardiac Pacing After 25 Years: A Practical Approach to Growing Complexity," Modern Cardiac Pacing, pp. 959–972 (1985).

S.A. Paul, J.M. Tencer, E.L. D'Amico, "Limb Length Evaluation Using the Electrodynogram, a Preliminary Report," Proc. $8^{th}$ Annual Mid–Atlantic Meeting of the American College of Sports Medicine Pennsylvania State University (Feb. 1985).

E.J. Perrins, W.M. Hudson, A. Labiri, E.B. Raftery, "A Randomised Controlled Trial of DDD and Incremental VVI Rate Responsive Pacing," JACC, vol. 3, No. 2, p. 507 (Feb. 1984).

E.V. Platia, "The Electrophysiologic Study," Management of Cardiac Arrhythmias: The Nonpharmacologic Approach, Chap. 5, pp. 62–98 (1987).

T.A. Preston, A.W. Preston, Jr., "The Automatic Rate Adjustment Pacemaker: The Possibilities of Rate Hysteresis," PACE, vol. 1, pp. 178–185 (Apr.–Jun. 1978).

D.R. Ramsdale, R.G. Charles, "Rate–Responsive Ventricular Pacing: Clinical Experience with the RS4–SRT Pacing System," PACE, vol. 8, pp. 378–386 (May/Jun. 1985, Part I).

Special Report of Joint American College of Cardiology/American Heart Association Task Force on Assessment of Cardiac Procedures, "Guidelines for Permanent Cardiac Pacemaker Implantation, May 1984," JACC, vol. 4, No. 2, pp. 434–442 (Aug. 1984).

A.F. Rickards, J. Norman, "Relation Between QT Interval and Heart Rate—New Design of Physiologically Adaptive Cardiac Pacemaker," British Heart Journal, vol. 45, pp. 56–61 (1981).

A.F. Rickards, R.M. Donaldson, "Rate Responsive Pacing," Clin. Prog. Pacing and Electrophysiol., vol. 1, No. 1, pp. 12–19 (1983).

A. Rickards, R. Donaldson, "Rate Responsive Pacing Using the QT Principle—Early Clinical Experience," J. Am. Coll. Cardiol., vol. 1, No. 2, p. 720 (1983).

A.F. Rickards, R.M. Donaldson, H.J. Th. Thalen, "The Use of QT Interval to Determine Pacing Rate: Early Clinical Experience," PACE, vol. 6, pp. 346–354 (Mar./Apr. 1983, Part II).

A.F. Rickards, R. M. Donaldson, "Rate Responsive Pacing Using the TX Pacemaker," VIIth World Symposium, PACE, vol. 6, p. A–12 (May 1983).

A.F. Rickards, "Non Atrial Synchronous Rate Responsive Pacing," Cardiac Pacing, Ch. 17, pp. 755–764 (1985).

A.F. Rickards, "Rate–Responsive Pacing," Modern Cardiac Pacing, Ch. 36, pp. 799–809 (1985).

A.F. Rickards, J.F. Godin, "Recommendations for Pulse Generator Clinical Evaluation," European Pacemaker Harmonization Study Group; Stimucoeur, vol. 14, No. 2, pp. 105–111 (1986).

A.F. Rickards, D.T. Connelly (on behalf of Topaz Study Group—Royal Brompton National Heart and Lung Hospital, U.K.), "Initial Experience with a New Single Chamber, Dual Sensor Rate Responsive Pacemaker," Cardiac Pacing/Exercise Testing, p. 225.

Ph. Ritter, J. Mugica, "Do we Really Need a Fully Automatic Pacemaker?" Eur. J.C.P.E., vol. 2, No. 2, p. A14 (Jun. 1991).

Ph. Ritter, L. Henry, K. Kunisada, S. Cazeau, J. Mugica, "Influence of Programming Settings of Fallback to Ensure 1:1 AV Association During Exercise in Patients with Complete AV Block Paced in DDD Mode with Chorus II Device," Cardio Stimolazione, vol. 10, No. 3, p. 235 (Sep. 1992).

S. Rogel, Y. Hazin, "Increased Excitability of the Heart Induced by Electrical Stimulation in the Absolute Refractory Period," CHEST, vol. 60, No. 6, pp. 578–582 (Dec. 1971).

M. Rosenqvist, H.O. Vallin, K.O. Edhag, "Rate Hysteresis Pacing: How Valuable Is It? A Comparison of the Simulation Rates of 70 and 50 Beats per Minute and Rate Hysteresis in Patients with Sinus Node Disease," PACE, vol. 7, pp. 332–340 (May/Jun. 1984, Part I).

P. Rossi, G. Rognoni, E. Occhetta, M.D. Prando, M. Minella, D.J. McCarter, "Hemodynamic Evaluation of Different Rate Responsive Pacings During Exercise," JACC, vol. 3, No. 2, p. 508 (Feb. 1984).

P. Rossi, G. Rognoni, F. Aina, E. Occhetta, "Permanent Physiological Pacing," G. Ital. Cardiol., vol. 14/II, pp. 784–787 (Oct. 1984).

P. Rossi, F. Aina, G. Rognoni, E. Occhetta, G. Plichi, M.D. Prando, "Increasing Cardiac Rate by Tracking the Respiratory Rate," PACE, vol. 7, pp. 1246–1256 (Nov./Dec. 1984, Part II).

P. Rossi, G. Plicchi, G. Canducci, G. Rognoni, F. Aina, "Respiration as a Reliable Physiological Sensor for Controlling Cardiac Pacing Rate," Br Heart J., vol. 51, pp. 7–14 (1984).

P. Rossi, G. Rognoni, E. Occhetta, F. Aina, M. D. Prando, G. Plicchi, M. Minella, "Respiration–Dependent Ventricular Pacing Compared with Fixed Ventricular and Atrial–Ventricular Synchronous Pacing: Aerobic And Hemodynamic Variables," JACC, vol. 6, No. 3, pp. 646–652 (Sep. 1985).

P. Rossi, "Biosensors: Reliability and Physiologic Specificity," Cardiac Pacing, pp. 765–770 (1985).

Round Table Discussion: "New Techniques for Establishing the Optimal Pacing Rate," PACE, vol. 6, pp. 508–510 (Mar./Apr. 1983, Part II).

Round Table Discussion: "Physiology of Dual–Chamber Pacing," PACE, vol. 6, pp. 355–356 (Mar./Apr. 1983, Part II).

L. Ryden, "Physiological Pacing: Pacemaker Selection," Cardiac Pacing: Electrophysiology and Pacemaker Technology, pp. 1413–1417 (1982).

N. Sadoul, J.P. Simon, B. Dodinot, E. Aliot (Department of Cardiology, Nancy University, France), "Ventricular Pacing Reduces Systolic Gradient in Obstructive Cardiomyopathy," Cardiac Pacing/Exercise Testing, p. 225.

D. Sailer, R. Kellner, W. Eberlein, G. Berg, "Kontinuierliche und Automatiche Registrierung von Glukose, pH und $pCO_2$," Biomedizinische Technik, vol. 21, pp. 195–196 (1976).

M. Sami, R. Ripley, "Medtronic Activitrax Pacemaker: Is It Truly Physiologic?" PACE, vol. 8, p. A–78 (May/Jun. 1985, Part II).

R.S. Sanders, U. Brunner, "Use of Pacemaker Diagnostic Data to Optimize DDDR Pacing," PACE, vol. 13, p. 1209 (Sep. 1990).

M. Santini, A. Alliegro, H. Ector, L. Rollies, A. Aubert, G.E. Antonioli, S. Sermasi, J. Mugica, J.P. Letouzey, M. Knudsen, D. Amundson, D.J. MacCarter, "Rate Responsive Pacing in Man at Various Levels of Activity," Cardiac Pacing, pp. 750–753 (1982).

J.G. Schindler, "Multiple Measurement System for the Electrochemical Analysis of Flowing Liquid and Gases," Biomedizinische Technik, vol. 22, pp. 235–243 (Oct. 1977).

M. Schluter, K.H. Kuck, K.P. Kunze, "Prevention of AV Nodal Tachycardia from Right Atrium by Programmed Stimulation," Circulation, Part II, vol. 70, No. 4, p. II–201 (Oct. 1984).

M.H. Schoenfeld, "Innovations of Programmable Functions in Dual Chamber Pacemakers," EUR, J.C.P.E., vol. 4, No. 2, p. 27 (Jun. 1994).

Seip.R. De Meersman, D. Snead, "Reliability Estimate of Exercise Left Ventricular Stroke Volume in Humans Using Impedance Cardiography," Proc. $8^{th}$ Annual Mid–Atlantic Meeting of the American College of Sports Medicine Pennsylvania State University (Feb. 1985).

D. Sellers, J. Knight, N. Fearnot, C. Laubach, W. Johnson, R. Shirey, D. Stevens, "Core Temperature Change with Exercise," Proc. $8^{th}$ Annual Mid–Atlantic Meeting of the American College of Sports Medicine Pennsylvania State University (Feb. 1985).

T.D. Sellers, N.E. Fearnot, W.L. Johnson, R.E. Shirey, D.A. Stevens, D.M. DiLorenzo, J.A. Knight, "Right Ventricular Blood Temperature Profiles for a Physiologic Pacing," Abstracts of the $58^{th}$ Scientific Sessions, p. III–433 (Nov. 1985).

T.D. Sellers, N. Fearnot, W. Johnson, R. Shirey, D. Stevens, "Central Venous Temperature Profiles for a Pacemaker Algorithm," PACE, vol. 8, Part II, p. 294 (Mar./Apr. 1985).

S. Sermasi, M. Marzaloni, M. Marconi, F. Cioppi, and M.A. Mainardi, "1986: Utilization of VVI Rate Responsive Pacing on the Grounds of 754 Consecutive VVI Pacemakers Implanted in 11 Italian Centers," PACE, vol. 13, p. 1210 (Sep. 1990).

R.Shanahan (St. Stephen's Hospital, Cork, Ireland), "Experience with the Siemens–Elema Variopacemaker," Nineteenth Annual Meeting of the International College of Angiology, Dublin, Ireland.

J.E. Shapland, D. MacCarter, B. Tockman, M. Knudson, "Physiologic Benefits of Rate Responsiveness," PACE, vol. 6, pp. 329–332 (Mar./Apr. 1983, Part II).

D.B. Shaw, C.A. Kekwick, A. Whistance, "Bradycardia Detecting Pacemakers: Scope in Diagnosis," VIIth World Symposium, PACE, vol. 6, No. 3, Part II, p. A–153 (May 1983).

B. Shively, N. Goldaschlager, "Progress in Cardiac Pacing," Arch. Intern. Med., vol. 145, pp. 2238–2244 (Dec. 1985).

J. Sholder, P.A. Levine, B.M. Mann, R.C. Mace, "Bidirectional Telemetry and Interrogation in Cardiac Pacing," The Third Decade of Cardiac Pacing, pp. 145–166 (1982).

I. Singer, D. Slater, C. Stavens, J. Kupersmith, "Effects of Ventricular Function on Survival in Patients with Automatic Implantable Cardioverter Defibrillator," PACE, vol. 12, p. 1210 (Sep. 1990).

E. Sowton, "New Frontiers in Clinical Pacing," Cardiac Pacing, pp. 373–374 (1982).

K. Stangl, A. Wirtzfeld, R. Heinze, K. Hoekstein, E. Alt, H.D. Liess, "Oxygen Content and Temperature of Mixed Venous Blood as Physiologic Parameters for Regulating Pacing Rate," PACE, vol. 8, p. A–21 (May/Jun. 1985, Part II).

K. Stangl, A. Wirtzfeld, R. Heinze, K. Hoekstein, E. Alt, H. D. Liess, "Oxygen Content and Temperature of Mixed Venous Blood as Physiological Parameters for Regulating Pacing Rate," Cardiac Pacing. Electrophysiology, Tachyarrhythmias, pp. 810–816 (1985).

K. Stangl, A. Wirtzfeld, O. Lochschmidt, R. Heinze, H. Blomer, Activity–Triggered Pacing: First Clinical Experiences with a New Activity Controlled Pacemaker (Sensulog 703); VIIth World Symposium, PACE, vol. 10, p. 746 (May–Jun. 1987, Part II).

N. Sulke, A. Dritsas, J. Chambers, E. Sowton, "Is Accurate Rate Response Programming Necessary?" PACE, vol. 13, pp. 1031–1044 (Aug. 1990).

R. Sutton, J. Perrins, P. Citron, "Physiological Cardiac Pacing," PACE, vol. 3, pp. 207–219 (Mar./Apr. 1980).

M.W. Sweesy, R.L. Batey, R.C. Forney, "Crosstalk During Bipolar Pacing," PACE, vol. 11, pp. 1512–1516 (Nov. 1988, Part I).

P.J. van Lake, P.A. Levine, G. A. Mouchawar, "Effect of Implantable Nonthoracotomy Defibrillation System on Permanent Pacemakers: An In Vitro Analysis with Clinical Implications," PACE, vol. 18, pp. 182–187 (Jan. 1995, Park II).

P.J. Vatterott, R.E. Vlietstra, D.L. Hayes, "DDD Pacing: Clinical Considerations," Mayo Clin. Proc., vol. 62, pp. 135–141 (Feb. 1987).

P. Vogt, J.J. Goy, M. Kuhn, P. Leuenberger, L. Kappenberger, "Single Versus Double Chamber Rate Responsive Cardiac Pacing: Comparison by Cardiopulmonary Noninvasive Exercise Testing," PACE, vol. 11, pp. 1896–1901 (Nov. 1988, Part II).

H. von Bibra, U. Busch, K. Stangl, A. Wirzfeld, "The Beneficial Effect of Short AV–Intervals in VDD Pacemaker Patients," PACE, vol. 8, Part II, p. A–69 (May/Jun. 1985, Part II).

B. Waldecker, J. Brachmann, U. Frees, R. Thorspecken, W. Kubler, "Hypersensitivity of the Carotis Sinus—Follow–up after Pacemaker–Implantation," PACE, vol. 9, p. 293 (Mar./Apr. 1986).

M.A. Warnowicz–Papp, "The Pacemaker Patient and the Electromagnetic Environment," Clin. Prog. in Pacing and Electrophysiol., vol. 1, No. 2, pp. 166–176 (1983).

J. Warren, J. Messenger, P. Belott, "A–V Interval Hysteresis: A Provision for Improved Tracking Behavior in a DDD Pacemaker," PACE, vol. 8, p. A–9 (May/Jun. 1985, Part II).

N. Wasty, D. Pantopoulos, S.T. Rothbart, L. Cohen, S. Saksena, "Detection of Sustained Ventricular Tachyarrhythmias Using Right Ventricular Hemodynamic Parameters: A Prospective Study," Journal of the American College of Cardiology, vol. 9, No. 2, Supplement A, p. 141A (Feb. 1987).

S.C. Webb, L.M. Lewis, J. Morris–Thurgood, A. Maseri (Royal Postgraduate Medical School, Hammersmith Hospital, London), "Comparative Assessment of Rate Responsive Pacemakers," PACE, vol. 10, p. 1232 (Sep./Oct. 1987).

M. Wehr, C.G. Schmitt, B. Noll, J. Krappe, P.M. Pittner, B.E. Strauer, "The Effect of Heart Rate and AV Interval on Left Ventricular Ejection Time (LVET) and Contractillity (PEP/LVET) in Patients with AV Universal Pacemakers," PACE, vol. 8, p. A–9 (May/Jun. 1985, Part II).

B.J. Whipp, J.A. Davis, F. Torres, K. Wasserman (Division of Respiratory Physiology and Medicine, Harbor–UCLA Medical Center, Torrance, California), "A Test to Determine Parameters of Aerobic Function During Exercise," Journal of Applied Physiology, vol. 50, pp. 217–221 (1981).

J.R. Windle, W.M. Miles, D.P. Zipes, E.N. Prystowsky, "Prolongation of Human Ventricular Refractoriness by Subthreshold Stimuli: Effect of Heart Rate, Pulse Width and Current Strength," Circulation, Part II, vol. 70, No. 4, p. II–201 (Oct. 1984).

A. Wirtzfeld, L. Goedel–Meinen, T. Bock, R. Heinze, H.D. Liss, J. Munteanu, "Central Venous Oxygen Saturation for the Control of Automatic Rate–Responsive Pacing," PACE, vol. 5, pp. 829–835 (Nov./Dec. 1982).

A. Wortzfeld, K. Stangl, R. Heinze, Th. Bock, H. D. Liess, E. Alt, "Mixed Venous Oxygen Saturation for Rate Control of an Implantable Pacing System," Cardiac Pacing, pp. 271–279 (1983).

A. Wirtzfeld, K. Stangl, R. Heinze, T. Bock, E. Alt, "An Active Optical Sensor for Monitoring Mixed Venous Oxygen Saturation for an Implantable Rate–Responsive Pacing System," PACE, vol. 6, p. A–12 (May 1983).

A. Wirtzfeld, R. Heinze, K. Stanzl, K. Hoekstein, E. Alt, H. D. Liess, "Regulation of Pacing Rate by Variations of Mixed Venous Oxygen Saturation," PACE, vol. 7, pp. 1257–1262 (Nov./Dec. 1984, Part II).

A. Wirtzfeld, K. Stangl, G. Schmidt, "Physiological Pacing: AV–Synchrony and Rate Control," Modern Cardiac Pacing, pp. 875–892 (1985).

M. Wish, R.D. Fletcher, J.S. Gottdiener, A.I. Cohen, J. Cutler, H. Rogers, "Hemodynamics of VVI and Physiologic Pacing," JACC, vol. 3, No. 2, p. 507 (Feb. 1984).

Y. Yamamoto, J. Sugai, "Atrial Contribution in VVI Pacing," PACE, vol. 6, No. 3, Part II, p. A0153 (May 1983).

F.I. Zacouto, L.J. Guize, "Fundamentals of Orthorhythmic Pacing," Cardiac Pacing: Diagnostic and Therapeutic Tools, pp. 213–218 (1976).

M. Zegelman, F. Beyersdorf, J. Kreuzer, N. Reifart, J. Happ, "Adaptation of Heart Rate to Exercise. Comparison of QT–Related and Respiratory Dependent Pacemakers," Progress In Clinical Pacing, pp. 104–110 (1984).

M. Zegelman, N. Treesek, P. Sammer, J. Kreuzer, S. Classen, E. Lichter, A. Werneyer, "The Belief in VVIR—An Illusion," Cardio Stimolazione, vol. 10, No. 3, p. 233 (Sep. 1992).

M. Zegelman, N. Reifart, J. Kreuzer, R. Wagner, B. Koch, "One Year of Clinical Experience With QT–Related Rate Responsive Pacemakers (Problems, Haemodynamic Long–Term Results)," (source unknown), pp. 847–852.

D.P. Zipes, E.N. Prystowsky, W.M. Miles, J.J. Heger, "Initial Experience with Symbios Model 7008 Pacemaker," PACE, vol. 7, pp. 1301–1305 (Nov./Dec. 1984, Part II).

F.T. Zugibe, N.C. Nanda, T. Akiyama, S.S. Barold, "Doppler Detection and Quantitation of Mitral Regurgitation During Ventricular and Atrioventricular Sequential Pacing," JACC, vol. 3, No. 2, p. 508 (Feb. 1984).

Intermedics Cardiac Pulse Generator Physician's Manual: COSMOS (Models 283–01V and 284–02V), Intermedics, Inc. (Jun. 1988).

Deltra TRS (Models 937/938 Type DDD, Dual–Chamber Pulse Generators): Physician's Manual, Cardiac Pacemakers, Inc. (Oct. 1988).

Delta T and Delta TRS (Model 2025 Software Module) Operator's Manual, Cardiac Pacemakers, Inc. (1988).

Intermedics Cardiac Pulse Generator Physician's Manual: COSMOS II (Models 283–03 and 284–05), Intermedics, Inc. (Dec. 1993).

Diamond Multisensor Dual Chamber Pacemaker: Reference Guide, Vitatron Medical B.V. (1993).

Intermedics Physician's Manual: COSMOS 3 Cardiac Pulse Generators, Intermedics, Inc. (Apr. 1996).

BIOrate RDP 3: Rate Responsive Pacemaker Controlled by Respiration, Biotec, Inc.

Summary Sheet QT; Summary Timeline of TX pacemaker, programmable parameters of the pacemaker, advantages and disadvantages of the pacemaker.

Topaz Automatic Dual Sensor Pacemaker Product Information, Vitatron, Inc.

Intermedics Product Technical Overview, Joe Vandegriff, Intermedics, Inc.

VIGOR DDD (Models 950 and 955 Pulse Generators) Physician's Manual.

"Defendants' Third Supplemental Response and Amended Response to Plaintiff's First Set of Interrogatories (Nos. 1–10)," served Jun. 20, 2003 by defendants in *Pacesetter, Inv. v. Cardiac Pacemakers, Inc. et al*, Civ. No. 02–1337 (D. Minn.).

R. Cowell, J. Morris–Thurgood, V. Paul, and C. Ilsley, "A Gold Standard for the Programming of Rate Adaptive Pacemakers: the Renaissance of the Sinus Mode," Cardio Stimolazione, vol. 10, No. 3, p. 235 (Dec. 1992).

A. Le Helloco, B. Lelong, M. Bedossa, V. Pasquali, M. Laurent, C. Almange, "Clinical Experience of an Acceleration Responsive Dual Chamber: Intermedics Relay Model 194–03," Cardio Stimolazione, vol. 10, No. 3, p. 240 (Dec. 1992).

NIPS Non–Invasive Programmed Stimulation: Summary of Controlled Market Release Study (Telectronics Pacing Systems)(Oct. 1994).

Telectronics 9602 Network Programmer Programming Guide (1997).

Cardiac Pacemakers, Inc. Delta Model 925 (Type DDD, Dual Chamber Pulse Generator) Physician's Manual.

Cardiac Pacemakers, Inc., Operator's Manual—VISTA/VISTA T Model 2057 Software Module.

Fletcher et al., "*The Use of the Implanted Pacemaker as an In Vivo Electrophysiology Laboratory,*" *Journal of Electrophysiology,* vol. 1, No. 5, pp 425–433 (1987).

Gillette, Case Study—NIPS Utilization for Atrial Flutter, Telectronics Pacing Systems (Mar. 1995).

Hassett et al., Noninvasive Diagnosis and Treatment of Atrial Flutter Utilizing Previously Implanted Dual Chamber Pacemaker, Pacing and Clinical Electrophysiology (PACE), vol. 11, No. 11, pp 1662–1666 (Nov. 1988—Part II).

Medtronic, Schrittmacherbeschreibung und Programmieranleitung (Anhang: Anwendung der Funktion EPU)—9886AG–Software, pp. i–x, 1–1—2–30 (Mar. 1996).

Medtronic, Pacemaker Information and Programming Guide (Supplement: Using the EPS Function)—9891A–Software, pp. i–x, 1–1—2–30 (May 1996).

Medtronic Launch Guide—Thera, Prodigy, Preva/Prevail (1995).

Telectronics Pacing Systems, NIPS Non–Invasive Programmed Stimulation—Stimulate . . . evaluate . . . terminate (Jan. 1995).

Telectronics Pacing Systems, NIPS Non–Invasive Programmed Stipulation—Quick Reference, pp. 1–28 (1995).

Wish et al., "*A New Advancement in Noninvasive Electrophysiology: A Standard Laboratory Stimulator Pulse Coupled with an Implanted Pacemaker,*" PACE, vol. 9, pp. 1089–1094 (Nov.–Dec. 1986—Part II).

"Defendants' Response to Plaintiff's First Set of Interrogatories (Nos. 1–10)," served Jun. 21, 2002 by defendants in *Pacesetter, Inc. v. Cardiac Pacemakers, Inc. et al,* Civ. No. 02–1337 (D. Minn.).

"Defendants' Supplemental Response to Plaintiff's First Set of Interrogatories (Nos. 1–10)," served Feb. 6, 2003 by defendants in *Pacesetter, Inc. v. Cardiac Pacemakers, Inc. et al,* Civ. No. 02–1337 (D. Minn.).

"Defendants' Second Supplemental Response to Plaintiff's First Set of Interrogatories (Nos. 1–10)," served May 2, 2003 by defendants in *Pacesetter, Inc. v. Cardiac Pacemakers, Inc. et al,* Civ. No. 02–1337 (D. Minn.).

Relay Models 293–03 and 294–03 User Manual, Intermedics, Inc. (1992).

Relay Models 293–03 and 294–03 Physician's Manual, Intermedics, Inc. (Dec. 1993).

Ventak PRxII (1715/1710) Physician's Manual, Cardiac Pacemakers, Inc.

Cadence Tiered Therapy Defibrillator System (V–100), Ventritex, Inc. (1993).

NIPS (Non–Invasive Programmed Stimulation Competitive Comparison, Telectronics Pacing Systems (2 pages).

Thera Fact Sheet, Medtronic, Inc. (1995).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4, 5, 20, 21, 26, 27, 42, and 43 are cancelled.

Claims 1, 11, 23 and 33 are determined to be patentable as amended.

Claims 2, 3, 6–10, 12–19, 22, 24, 25, 28–32, 34–41 and 44, dependent on an amended claim, are determined to be patentable.

New claims 45–75 are added and determined to be patentable.

1. An implantable cardiac stimulating device, comprising:
   means for performing electrophysiological testing in a first chamber of a heart;
   means for determining if said electrophysiological testing of the first chamber of the heart is being performed; and
   means for providing bradycardia pacing support in a second chamber of the heart while electrophysiological testing is being performed in the first chamber of the heart;
   *wherein the providing means comprises means for providing demand pacing support.*

11. An implantable dual-chamber pacemaker for performing electrophysiological testing in an atrial chamber of a patient's heart while maintaining ventricular pacing support, the pacemaker capable of telemetric communication with an external programmer, the pacemaker comprising:
   telemetry means for receiving commands from the external programmer;
   atrial pulse generating means for providing atrial stimulation pulses to an atrial chamber of the patient's heart;
   ventricular pulse generating means for providing ventricular stimulation pulses to a ventricular chamber of the patient's heart; and
   control means for causing the atrial pulse generating means to generate the atrial stimulation pulses in a sequence for performing electrophysiological testing in the atrial chamber and for causing the ventricular pulse generating means to generate the ventricular stimulation pulses to treat bradycardia in the ventricular chamber while the atrial stimulation pulses are being generated in a sequence for performing electrophysiological testing in the atrial chamber;
   *wherein the control means causes the ventricular pulse generating means to provide demand pacing support.*

23. A method of performing noninvasive electrophysiological testing using an implantable cardiac stimulating device, comprising the steps of:
   performing electrophysiological testing a first chamber of a heart using the implantable cardiac stimulating device; and
   providing bradycardia pacing in a second chamber of the heart using the implantable cardiac stimulating device while the step of electrophysiological testing proceeds in the first chamber of the heart;
   *wherein the providing step comprises providing demand pacing support.*

33. A method of using an implantable dual-chamber pacemaker for performing electrophysiological testing in an atrial chamber of a patient's heart while maintaining ventricular pacing support, the pacemaker having an atrial sense amplifier and a pulse generator and a ventricular sense amplifier and a ventricular pulse generator, the pacemaker in telemetric communication with an external programmer for receiving commands therefrom, comprising the steps of:
   using the atrial pulse generator of the pacemaker to provide atrial stimulation pulses to an atrial chamber of the patient's heart;
   using the ventricular pulse generator of the pacemaker to provide ventricular stimulation pulses to a ventricular chamber of the patient's heart;
   controlling the atrial pulse generator to generate the atrial stimulation pulses in a sequence for performing electrophysiological testing in the atrial chamber; and
   controlling the ventricular pulse generator to generate the ventricular stimulation pulses to treat bradycardia in the ventricular chamber while the atrial stimulation pulses are being generated in a sequence for performing electrophysiological testing in the atrial chamber;
   *wherein the step of controlling the ventricular pulse generator comprises causing the ventricular pulse generator to provide demand pacing support.*

*45. The implantable cardiac stimulating device of claim 1, comprising:*
   *a second means for providing bradycardia pacing support to the second chamber of the heart, wherein:*
      *the providing means provides electrical stimulation to the second chamber of the heart in accordance with a first set of predetermined parameters having a first set of parameter values; and*
      *the second providing means provides electrical stimulation to the second chamber of the heart in accordance with a second set of predetermined parameters having a second set of parameter values when the determining means determines that electrophysiological testing is not being performed in the first chamber of the heart.*

*46. The implantable cardiac stimulating device of claim 45, wherein the first and second sets of parameters include parameters selected from the group consisting of pulse width, pulse amplitude, pacing rate, blanking interval and amplifier sensitivity.*

*47. The implantable cardiac stimulating device of claim 45, wherein the second providing means provides bradycardia pacing support in a demand mode of operation.*

*48. The implantable cardiac stimulating device of claim 45, wherein the second providing means provides bradycardia pacing support in a triggered mode of operation.*

*49. The implantable cardiac stimulating device of claim 45, wherein the second providing means provides bradycardia pacing support in an asynchronous mode of operation.*

*50. The implantable cardiac stimulating device of claim 1, comprising:*
   *means to sense activity in the second chamber of the heart while electrophysiological testing is being performed in the first chamber of the heart; and*
   *means to desensitize the sense means while electrophysiological testing is being performed in the first chamber of the heart.*

51. The implantable cardiac stimulating device of claim 50, wherein the means to desensitize the sense means comprises means to provide a blanking signal to the sense means.

52. The implantable cardiac stimulating device of claim 50, wherein the means to desensitize the sense means comprises means to adjust a sensitivity level of the sense means.

53. An implantable cardiac stimulating device, comprising:

means for performing electrophysiological testing in a first chamber of a heart;

means for determining if said electrophysiological testing of the first chamber of the heart is being performed;

means for providing bradycardia pacing support in a second chamber of the heart while electrophysiological testing is being performed in the first chamber of the heart; and means for sensing signals from the second chamber of the heart while the providing means is operative.

54. The implantable cardiac stimulating device of claim 53, wherein the performing means performs electrophysiological testing in an atrial chamber of the heart.

55. The implantable cardiac stimulating device of claim 53, wherein the providing means provides bradycardia pacing support in a ventricular chamber of the heart.

56. The implantable cardiac stimulating device of claim 53, wherein the providing means comprises means for providing demand pacing support.

57. The implantable cardiac stimulating device of claim 53, wherein the providing means comprises means for providing triggered pacing support.

58. The implantable cardiac stimulating device of claim 53, wherein the performing means comprises means for administering electrical stimulation to the first chamber of the heart to induce a cardiac arrhythmia.

59. The implantable cardiac stimulating device of claim 53, wherein the performing means comprises means for administering electrical stimulation to the first chamber of the heart to revert a cardiac arrhythmia.

60. The implantable cardiac stimulating device of claim 53, wherein:

the performing means comprises means for administering electrical stimulation to the first chamber of the heart in accordance with a first set of predetermined parameters having a first set of parameter values; and the providing means comprises means for administering electrical stimulation to the second chamber of the heart in accordance with a second set of predetermined parameters having a second set of parameter values.

61. The implantable cardiac stimulating device of claim 60, wherein the first and second sets of parameters include parameters selected from the group consisting of pulse width, pulse amplitude, pacing rate, blanking interval and amplifier sensitivity.

62. The implantable cardiac stimulating device of claim 53, further comprising means for providing marker data for activity in the first chamber and the second chamber of the heart.

63. The implantable cardiac stimulating device of claim 53, comprising:

a second means for providing bradycardia pacing support in the second chamber of the heart, wherein:

when the determining means determines that electrophysiological testing is being performed in the first chamber of the heart, the performing means administers electrical stimulation to the second chamber of the heart in accordance with a first set of predetermined parameters having a first set of parameter values; and when the determining means determines that electrophysiological testing is not being performed in the first chamber of the heart, the second performing means administers electrical stimulation to the second chamber of the heart in accordance with a second set of predetermined parameters having a second set of parameter values.

64. The implantable cardiac stimulating device of claim 63, wherein the first and second sets of parameters include parameters selected from the group consisting of pulse width, pulse amplitude, pacing rate, blanking interval and amplifier sensitivity.

65. The implantable cardiac stimulating device of claim 53, wherein the second providing means provides bradycardia pacing support in a demand mode of operation.

66. The implantable cardiac stimulating device of claim 53, wherein the second providing means provides bradycardia pacing support in a triggered mode of operation.

67. The implantable cardiac stimulating device of claim 53, wherein the second providing means provides bradycardia pacing support in an asynchronous mode of operation.

68. The implantable cardiac stimulating device of claim 53, comprising means for desensitizing the sensing means.

69. The implantable cardiac stimulating device of claim 68, wherein the means for desensitizing the sensing means comprises means to provide a blanking signal to the sensing means.

70. The implantable cardiac stimulating device of claim 68, wherein the means for desensitizing the sensing means comprises means to adjust a sensitivity level of the sensing means.

71. An implantable dual-chamber pacemaker for performing electrophysiological testing in an atrial chamber of a patient's heart while maintaining ventricular pacing support, the pacemaker capable of telemetric communication with an external programmer, the pacemaker comprising:

telemetry means for receiving commands from the external programmer;

atrial pulse generating means for providing atrial stimulation pulses to an atrial chamber of the patient's heart;

ventricular pulse generating means for providing ventricular stimulation pulses to a ventricular chamber of the patient's heart;

control means for causing the atrial pulse generating means to generate the atrial stimulation pulses in a sequence for performing electrophysiological testing in the atrial chamber and for causing the ventricular pulse generating means to generate the ventricular stimulation pulses to treat bradycardia in the ventricular chamber while the atrial stimulation pulses are being generated in a sequence for performing electrophysiological testing in the atrial chamber;

further comprising ventricular sensing means coupled to the control means for sensing cardiac events in the ventricular chamber during electrophysiological testing in the atrial chamber; and wherein the control means desensitizes the ventricular sensing means to atrial stimulation pulses generated by the atrial pulse generating means during electrophysiological testing.

72. The pacemaker of claim 71, wherein the control means provides a blanking signal, wherein the blanking signal when applied thereto, desensitizes the ventricular sensing means.

73. The pacemaker of claim 71, wherein the ventricular sensing means comprises amplifier means, and the control means desensitizes the ventricular sensing means by reducing the sensitivity of the amplifier means.

74. A method of using an implantable dual-chamber pacemaker for performing electrophysiological testing in an atrial chamber of a patient's heart while maintaining ventricular pacing support, the pacemaker having an atrial sense amplifier and a pulse generator and a ventricular sense amplifier and a ventricular pulse generator, the pacemaker in telemetric communication with an external programmer for receiving commands therefrom, comprising the steps of:

using the atrial pulse generator of the pacemaker to provide atrial stimulation pulses to an atrial chamber of the patient's heart;

using the ventricular pulse generator of the pacemaker to provide ventricular stimulation pulses to a ventricular chamber of the patient's heart;

controlling the atrial pulse generator to generate the atrial stimulation pulses in a sequence for performing electrophysiological testing in the atrial chamber;

controlling the ventricular pulse generator to generate the ventricular stimulation pulses to treat bradycardia in the ventricular chamber while the atrial stimulation pulses are being generated in a sequence for performing electrophysiological testing in the atrial chamber;

further comprising the step using the ventricular sense amplifier to sense cardiac events in the ventricular chamber; and further comprising the step of desensitizing the ventricular sense amplifier to atrial stimulation pulses generated by the atrial pulse generator during electrophysiological testing.

75. The method of claim 74, wherein the desensitizing step comprises providing a blanking signal to the ventricular sense amplifier.

* * * * *